(12) United States Patent
Honigsbaum

(10) Patent No.: US 10,327,889 B2
(45) Date of Patent: Jun. 25, 2019

(54) TENSIONING RINGS FOR ANTERIOR CAPSULES AND ACCOMMODATIVE INTRAOCULAR LENSES FOR USE THEREWITH

(71) Applicant: Richard F. Honigsbaum, Passaic, NJ (US)

(72) Inventor: Richard F. Honigsbaum, Passaic, NJ (US)

(*) Notice: Subject to any disclaimer, the term of this patent is extended or adjusted under 35 U.S.C. 154(b) by 0 days.

(21) Appl. No.: 14/768,994

(22) PCT Filed: Feb. 27, 2014

(86) PCT No.: PCT/US2014/019016
§ 371 (c)(1),
(2) Date: Aug. 19, 2015

(87) PCT Pub. No.: WO2014/134302
PCT Pub. Date: Sep. 4, 2014

(65) Prior Publication Data
US 2016/0000558 A1    Jan. 7, 2016

Related U.S. Application Data

(60) Provisional application No. 61/770,446, filed on Feb. 28, 2013.

(51) Int. Cl.
*A61F 2/16* (2006.01)
(52) U.S. Cl.
CPC .......... *A61F 2/1694* (2013.01); *A61F 2/1624* (2013.01); *A61F 2/1648* (2013.01);
(Continued)

(58) Field of Classification Search
CPC .............................. A61F 2/147; A61F 2/1694
See application file for complete search history.

(56) References Cited

U.S. PATENT DOCUMENTS

| 4,080,709 A | * | 3/1978 | Poler ......................... A61F 2/16 216/100 |
| 4,718,905 A | * | 1/1988 | Freeman ................. A61L 27/30 427/2.24 |

(Continued)

FOREIGN PATENT DOCUMENTS

| EP | 0 478 929 | 4/1992 |
| WO | WO 00/30566 | 6/2000 |

OTHER PUBLICATIONS

Office Action dated Jul. 26, 2016 which issued in the corresponding Canadian Patent Application No. 2,902,075.

(Continued)

*Primary Examiner* — Leslie Lopez
(74) *Attorney, Agent, or Firm* — Cozen O'Connor

(57) ABSTRACT

A tensioning device for attaching to the anterior capsule of an eye, and accommodative intraocular lens systems employing the device. The tensioning device includes a biocompatible, elastically reconfigurable ring for restoring at least a portion of the anterior capsule centripetal forces lost by capsulorhexis. The tensioning device also includes a plurality of penetrators configured for attaching the ring to the anterior capsule. The plurality of penetrators is biocompatible with the eye and partially embedded in a part of the ring configured for facing the anterior capsule.

14 Claims, 12 Drawing Sheets

(52) U.S. Cl.
CPC ............... *A61F 2002/1681* (2013.01); *A61F 2002/1689* (2013.01); *A61F 2210/0014* (2013.01); *A61F 2210/0057* (2013.01); *A61F 2220/0008* (2013.01); *A61F 2220/0016* (2013.01); *A61F 2230/0006* (2013.01); *A61F 2230/0034* (2013.01); *A61F 2230/0065* (2013.01)

(56) References Cited

U.S. PATENT DOCUMENTS

| | | | | |
|---|---|---|---|---|
| 4,722,867 | A | * | 2/1988 | Halpern ............... A61L 27/34 428/476.6 |
| 5,628,795 | A | * | 5/1997 | Langerman ............ A61F 2/14 623/4.1 |
| 6,106,642 | A | * | 8/2000 | DiCarlo ............... C22F 1/006 148/563 |
| 6,413,277 | B1 | | 7/2002 | Neuhann |
| 2007/0032867 | A1 | | 2/2007 | Cumming |
| 2007/0088433 | A1 | * | 4/2007 | Esch ................ A61F 2/1635 623/6.13 |
| 2009/0234449 | A1 | | 9/2009 | Juan, Jr. |
| 2010/0204790 | A1 | | 8/2010 | Whitsett |
| 2012/0232649 | A1 | | 9/2012 | Cuevas |

OTHER PUBLICATIONS

International Preliminary Report on Patentability dated Sep. 11, 2015 for corresponding PCT application No. PCT/US2014/019016.

* cited by examiner

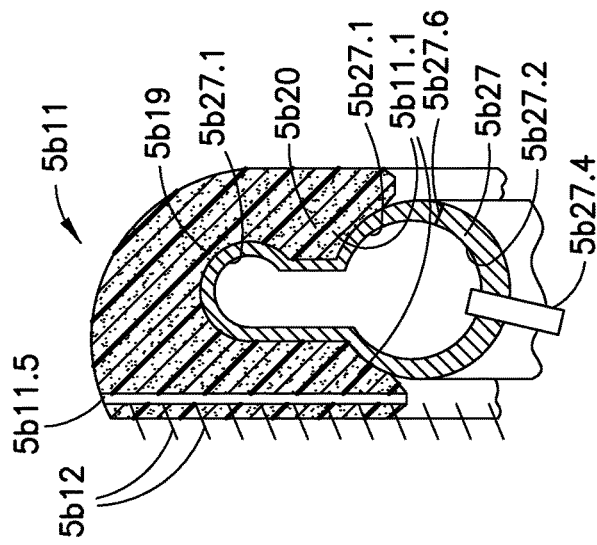
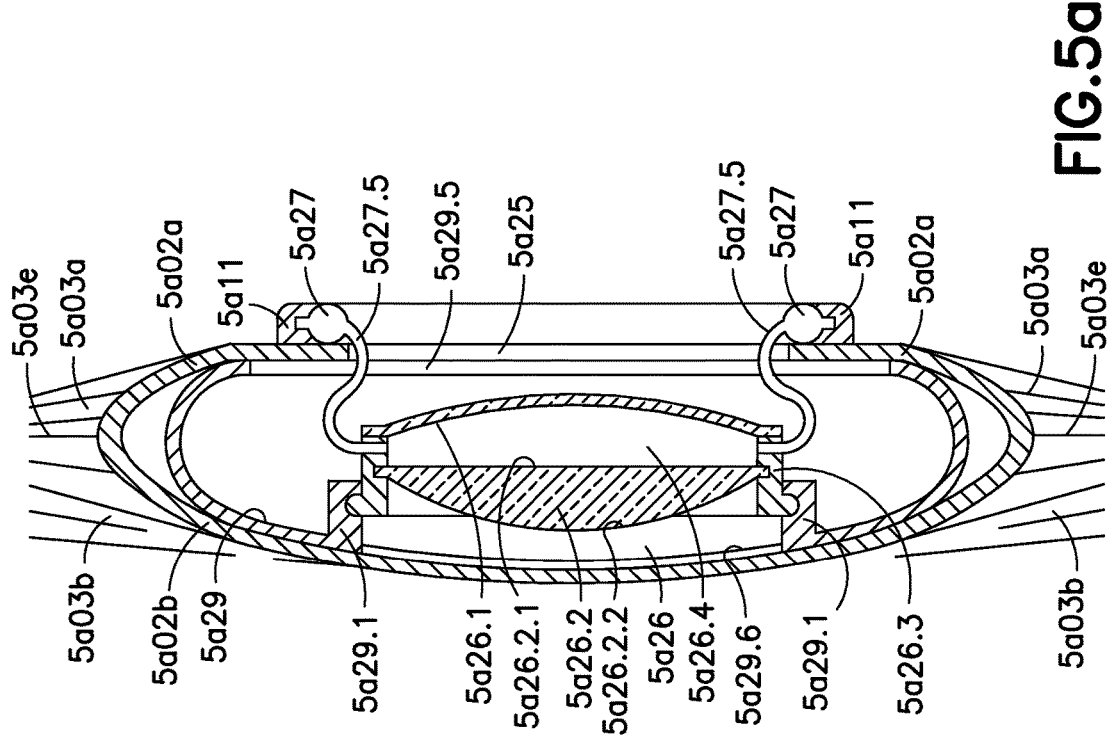

TENSIONING RINGS FOR ANTERIOR CAPSULES AND ACCOMMODATIVE INTRAOCULAR LENSES FOR USE THEREWITH

CROSS-REFERENCE TO RELATED APPLICATIONS

This is a U.S. national stage of application No. PCT/EP2014/019016, filed on Feb. 27, 2014. This application claims the benefit under 35 U.S.C. § 119(e) of U.S. Provisional Patent Application Ser. No. 61/770,446, filed on Feb. 28, 2013, which is incorporated by reference herein in its entirety.

FIELD OF THE INVENTION

The present invention relates to tensioning rings for anterior capsules and accommodative intraocular lenses for use therewith, and to methods for implanting the tensioning rings and intraocular lenses. Specifically, the present invention relates to tensioning rings for attachment to anterior capsules to restore the centripetal forces that were provided by the portion of anterior capsules removed by capsulorhexis, to accommodative intraocular lenses that are directly or indirectly actuated by the rings, and to methods for implanting the lenses and the rings.

DISCUSSION OF BACKGROUND ART

Prior art intraocular lenses, whether accommodative or single-focus, are typically implanted in the capsule of an eye from which the crystalline lens has been removed via a procedure that includes capsulorhexis. Because the capsulorhexis destroys the natural accommodation mechanism of the eye whereby the crystalline lens is elastically reconfigured to a diopter power appropriate for the visual task by the posterior forces exerted by the anterior capsule and the anterior forces exerted by the posterior capsule, the visual accommodation must be provided in some other way.

Because the crystalline lens is also both a spacer between the anterior and posterior capsules and a determinant of the zonule-proximal capsule curvature, and thus a determinant of the zonular load distribution in the natural eye, these crystalline lens functions, which are lost by its extraction, must also be addressed. Most of the accommodative intraocular lenses in the prior art assume the validity of the Helmholtz Theory of Accommodation—i.e., that tension on the zonules increases the equatorial diameter of the capsule and flattens the capsule, and thus flattens the crystalline lens therein to a shape appropriate for a distant vision, while contraction of the ciliary body muscle(s) reduces zonular tension and allows the elastically reconfigurable crystalline lens to assume a more convex (accommodative) shape. Thus, lens assemblies implanted in capsules and having accommodating mechanisms responsive to these changes in diameter should be able to provide the visual accommodation despite the capsulorhexis.

The prior art includes tens, if not hundreds, of examples of lenses intended to provide accommodation on this basis. Most of these lenses can be demonstrated to work as expected in vitro. None of the lenses, however, work as expected in vivo. For example, the named inventors of U.S. Patent Application Publication Nos. 2009/0234449 (De Juan, Jr., et al.) and 2007/0100445 (Shadduck), attribute this failure to "shrink-wrapping," and disclose spacers intended to prevent this failure by maintaining a separation of the anterior and posterior capsules. While "shrink-wrapping" may be a contributing factor to this failure, its elimination has not solved the problem.

There are, however, two kinds of prior art intraocular lenses that can be implanted in capsulorhexis-crippled capsules that provide some degree of accommodation. One is a Fresnel configuration that is disclosed in U.S. Patent Application Publication No. 2007/0171362 (Simpson). ReStor™, ReZoom™ and Tecris™ are known trade names for such lenses. These lenses are not intended to respond to a change in capsular diameter, but instead have zones of different diopter power, some of which are appropriate for distance vision and others for reading. The well-known shortcomings of such lenses, however, include loss of contrast, halos, etc.

The other is an intraocular lens assembly that is disclosed in U.S. Pat. No. 6,849,091 to Cumming and other U.S. Patents and published U.S. Patent Applications by the same inventor ("Cumming"). Crystalens™ is a known trade name for such lens assemblies. These intraocular lens assemblies are anchored equatorially in capsulorhexis-crippled capsules by "shrink-wrapping," and accommodation is provided by anterior movement of the lens in response to forces exerted anteriorly upon the portion of the lens assembly that is in contact with the posterior capsule. Cumming attributes these forces to "viscous pressure" from the vitreous humor. Thus the Crystalens™, which achieves some degree of visual accommodation, does so in direct opposition to Helmholtz, who teaches disaccommodation via flattening of the capsule—i.e., anterior translation of the posterior capsule. De Juan, Jr. also discloses the use of "viscous pressure" to provide the visual accommodation.[6]

U.S. Patent Application Publication No. 2007/0032867 to Cumming discloses translational accommodative intraocular lenses having plate-type haptics with "T" shaped ends, and U.S. Pat. No. 7,985,253 to the same inventor discloses hydraulic accommodative intraocular lenses in which the "T" shaped ends are curly. Plate-type haptics are familiar from commercially available intraocular lenses, and both the "T" shaped and the curly ends are variations of the "J" type haptics familiar from the prior art that, like the "J" type haptics, secure the lens to the capsule by the "shrink-wrapping" of the latter.

U.S. Pat. No. 2,300,251 to Flint discloses variable focus hydraulic lenses of the kind employed by Cumming's hydraulic lens systems, and U.S. Pat. No. 4,261,655 to Honigsbaum teaches eyeglasses having adjustable focus hydraulic lenses in which a part of the focusing mechanism is a bellows-like arrangement.

U.S. Patent Application Publication No. 2011/0035001 to Woods discloses spacer-like "optics positioning members" that are implanted into capsules and that are intended to provide the visual accommodation by appropriately positioning lens elements in response to zonular tension-induced changes in capsule shape, and are expected to do so despite the unaddressed crippling effects of capsulorhexis.

U.S. Patent Application Publication No. 2012/0253459 to Reich, et al. discloses a lens elastically reconfigured by means in direct contact with the ciliary structure of the eye.

U.S. Patent Application Publication No. 2007/0123981 to Tassignon ("Tassignon") discloses the use of a ring as a guide or template for cutting an axisymmetric capsulorhexis as a part of a procedure for intraocular lens implantation, and a two part intraocular lens arrangement in which a "U" section haptic ring embraces the margin of both an anterior and posterior capsulorhexis holds a lens that is separable from its haptic ring. Tassignon also states that such an arrangement can provide accommodation on the basis of changes in the capsular diameter.

U.S. Pat. No. 4,822,360 to Deacon, U.S. Pat. No. 7,156,101 to Terwee, and U.S. Patent Application Publication No. 2012/0226351 to Peyman disclose intracapsular lenses intended to replace the natural crystalline lens. Because the implantation of such lenses in a fully functional state would require an unacceptably large corneal incision, the patents disclose implantation of the lens as an uncured polymer that is to be cured and shaped in vivo. The patents do not, however, disclose how the lens-shaping function of the anterior capsule compromised by capsulorhexis during the removal of the natural lens is restored.

U.S. Patent Application Publication No. 2012/0303118 to DeBoer, et al. ("DeBoer") discloses a bag-type crystalline lens replacement that is implanted uninflated via a small equator-proximal anterior capsule incision that is also used for lensectomy. The lens is then "inflated" with silicone oil to the desired size and shape. DeBoer also discloses a plurality of self-sealing post-implantation bag access ports. Such ports are familiar from known art, such as spray-can valves.

U.S. Patent Application Publication No. 2007/0213817 to Esch, et al. discloses hydraulic lens assemblies having tubular ring haptics in which a portion of the actuating fluid is contained.

Surgical glues are commercially available under trade names such as BioGlue™, TissueGlu™, etc., and U.S. Patent Application Publication No. 2011/0029074 to Reisin, et al. discloses alternatives to the commercially available surgical glue products.

U.S. Patent Application Publication No. 2013/0013061 to Coroneo ("Coroneo") discloses a "U" section ring for permanent insertion into a capsulorhexis to apply centrifugal forces to capsulorhexis-crippled anterior or posterior capsules to address phimosis. Tassignon [13] discloses a similar section ring for centrifugal forces but for a different purpose. While Coroneo uses the term "capsular tension rings" (CTR), Coroneo's CTRs are the familiar "C" shaped rings inserted into some capsules to apply centrifugal forces to address phimosis. Such CTRs are available commercially from FCI Opthalmics and others, and, like the Coroneo ring, apply centrifugal forces to the capsule.

U.S. Patent Application Publication No. 2013/0304206 to Pallikaris, et al. ("Pallikaris") discloses zonules that originate at the ciliary body muscle and insert both anteriorly and posteriorly at the equatorial region of the capsule, thus centrifugally tensioning the capsule. Pallikaris also discloses that, if the centripetal equatorial capsular tension lost by capsulorhexis and crystalline lens removal were restored, the decrease in zonular tension resulting from contraction of the ciliary body muscle would decrease the capsule diameter, and that this change in capsular diameter could actuate an accommodative intraocular lens.

Pallikaris further discloses three mechanisms to restore the centripetal tension: (1) a tensioning ring glued equatorially to the capsule interior, (2) a comb-like equatorial compression ring the tines of which are implanted between the zonules, and (3) an interior capsule equator tensioning ring held in place by clamps and/or grooves that secure a further surgically modified anterior capsule to the ring.

Capsules are of course soft tissue, and lens implants are expected to serve the patient for the rest of his/her life—i.e., for two decades or more, and there are no soft tissue glues that can serve their intended purpose for anywhere near this length of time.

There are about 72 zonules, roughly half anterior and half posterior, and implanting anywhere near this complement of compression ring tines between both anterior and posterior zonules without damage to the zonules and/or the tines is a virtually impossible task.

The three mechanisms for restoring centripetal tensions are based upon the assumption that the zonules originate at the ciliary body muscle and insert both anteriorly and posteriorly at the equatorial region of the capsule. Both in-vivo studies (e.g., "Extralenticular and Lenticular Aspects of Accommodation and Presbyopia in Human vs. Monkey Eyes," IOVS Manuscript, IOVS 12-10846, Jun. 6, 2013 by M. A. Croft, et al. ("Croft")) and in-vitro studies (e.g., "Evidence for Posterior Zonular Fiber Attachment on the Anterior Hyaloid Membrane," IOVS Vol. 47, No. 11, November 2006 by Bernal, et al. ("Bernal")) confirm, however, that at least some of the zonules originate elsewhere on the ciliary body, and also confirm that at least some of the posterior zonules insert at the hyaloid membrane before inserting at the posterior capsule. Thus, the change in zonular tension moves the capsule equator anteriorly and posteriorly with respect to the tensioning device or rotates the tensioning devise about the axis of its cross-section, or both.

This applies peel-type loading to the glued version (which is the kind of loading to which glue bonds are most vulnerable), a saw-type motion to the tines of the comb-like version (which can cut the zonules and/or the tines), and accommodation when disaccommodation is expected (and vice versa) when a surgically modified anterior capsule is attached to a capsule-equator-based tensioning ring.

The Croft and Bernal studies are of particular interest because they both offer evidence that at least some, if not all, of the posterior zonules insert at the anterior hyaloid membrane before inserting at the posterior capsule. Thus, the anterior translation of the posterior capsule is constrained while the anterior capsule is free to translate posteriorly in response to anterior zonule tension because the anterior zonules insert directly at the anterior capsule. This not only explains the visual accommodation mechanism of the human eye, which is a combination of translation and elastic reconfiguration, but it also explains the need to restore the centripetal anterior capsule forces lost by capsulorhexis if the accommodative intraocular lenses of this invention and/or those of the prior art are to serve their intended function.

SUMMARY OF THE INVENTION

This invention addresses the accommodative failures of prior art intraocular lenses with a tensioning ring that is attached to the anterior capsule to restore the centripetal anterior capsular forces lost by capsulorhexis. These centripetal forces are opposed by the centrifugal forces exerted by the zonules, and the latter forces are increased and decreased by the relaxation and contraction of the ciliary body muscle(s), respectively. Thus, the anterior capsular forces are restored to their pre-capsulorhexis levels, and these restored forces are directly and/or indirectly used to actuate an accommodative intraocular lens assembly implanted in the capsule. Suitably modified accommodative intraocular lens assemblies can alternately be implanted for actuation by the change in tensioning ring diameter rather than by forces exerted by the capsule.

This invention also includes a spacer to maintain separation between the anterior and the posterior capsule and to restore at least some of the equator-proximal capsule curvature and thus the zonular load distribution lost by crystalline lens extraction. Spacers also actuate the accommodative mechanism of the lenses of some versions of this invention, and serve as a mounting and support structure for the lenses of others.

In one embodiment, a tensioning device configured for attaching to the anterior capsule of an eye is provided. The tensioning device includes a biocompatible, elastically reconfigurable ring for restoring at least a portion of anterior capsule centripetal forces lost by capsulorhexis. The tensioning device also includes a plurality of penetrators configured for attaching the ring to the anterior capsule. The plurality of penetrators is biocompatible and partially embedded to a part of the ring configured for facing the anterior capsule.

In another embodiment, a tensioning ring is configured for attaching to the anterior face of a shrink-wrapped capsule for securing a replacement intraocular lens or an augmentation intraocular lens to the capsule. The tensioning ring includes a plurality of penetrators that are partially embedded in a part of the ring configured for facing the shrink-wrapped capsule. The tensioning ring also includes a substantially axisymmetric groove in a part of the ring proximal to the ring's principal axis. The groove is configured for initially holding an expander ring and for permanently holding the haptics of a replacement or an augmentation intraocular lens. The ring is made of a biocompatible, elastically reconfigurable polymer.

In yet another embodiment, a biocompatible accommodative intraocular lens system is provided. The lens system includes a tensioning ring that is configured for attaching to the anterior capsule of an eye to restore at least a part of anterior capsule centripetal forces lost by capsulorhexis. The lens system also includes a foldable accommodative intraocular lens assembly that is configured for implantation into the capsule of the eye to restore at least a portion of normal vision to the eye. The lens system further includes a foldable spacer-actuator that is configured for implantation in the capsule to maintain separation between the anterior capsule and the posterior capsule of the eye and to translate the accommodative intraocular lens system. The foldable spacer-actuator, may be attached to the lens assembly. It may also be an integral part of the lens assembly.

In another embodiment, a biocompatible accommodative intraocular lens system is provided. The lens system includes a grooved tensioning ring configured for attaching to the anterior capsule of an eye to restore at least a portion of the centripetal forces lost by capsulorhexis. The lens system also includes a foldable hydraulic accommodative intraocular lens assembly configured for implantation in the capsule to restore at least a portion of normal vision to the eye and a ring-type hydraulic actuator for implantation in the tensioning ring groove to change the diopter power of the hydraulic intraocular lens assembly. The lens system further includes a foldable spacer configured for maintaining a separation between an anterior portion and a posterior portion of the capsule of the eye, and for holding the hydraulic intraocular lens assembly.

In another embodiment, a method is provided for implanting an accommodative intraocular lens system into an eye to replace a cataractous or otherwise compromised crystalline lens, wherein the intraocular lens system comprises a grooved anterior capsule tensioning ring for attaching to the anterior capsule of the eye and one of a capsule-equator-anchored accommodative intraocular lens assembly with a spacer-actuator and a spacer-based accommodative intraocular lens assembly with a spacer. The method includes the steps of preparing the eye for capsulorhexis and injecting into the eye the tensioning ring. An expander ring has been inserted into a groove of the tensioning ring. The method also includes the steps of expanding the tensioning ring to a diameter that provides the ring centripetal forces to be applied to the anterior capsule after implantation of the lens assembly and one of the spacer-actuator and spacer. The method further includes the steps of positioning the tensioning ring substantially axisymmetrically on the anterior capsule and attaching the tensioning ring to the anterior capsule by reducing the expander ring pressure. The method also includes the steps of cutting a substantially axisymmetric capsulorhexis, adjusting the expander ring pressure to a level corresponding to anterior capsule centripetal forces safe for the zonules of an empty capsule, and extracting the crystalline lens. The method also includes the steps of purging the surgical debris from the capsule and the eye, implanting one of the lens assembly with the spacer-actuator and the lens assembly with the spacer into the capsule, and depressurizing the expander ring and removing it from the eye.

In another embodiment, a method for securing one of a replacement intraocular lens assembly and an augmenting intraocular lens assembly to the anterior face of the shrink-wrapped capsule of an eye is provided. The method includes the steps of preparing the eye as for a cataract surgery, and injecting a grooved tensioning ring having an expander ring into the eye. The method also includes the steps of expanding the tensioning ring to a diameter that provides a desired ring centripetal force and positioning the tensioning ring axisymmetrically against the anterior face of the shrink-wrapped capsule. The method further includes the steps of reducing the expander ring pressure to attach the grooved tensioning ring to the anterior face of the shrink-wrapped capsule, depressurizing the expander ring, and removing it from both the grooved tensioning ring and the eye. The method also includes the steps of injecting one of the replacement intraocular lens assembly and the augmenting intraocular lens assembly into the eye, and inserting the haptics of the lens assembly into the tensioning ring groove.

Other features and advantages of the present invention will become apparent from the following more detailed description, taken in conjunction with the accompanying drawings, which illustrate, by way of example, the principles of the presently described apparatus and methods of its use.

BRIEF DESCRIPTION OF THE DRAWINGS

The following description, given with respect to the attached drawings, may be better understood with reference to the non-limiting examples of the drawings, wherein:

FIGS. 5a-5d are sectional views of spacer-anchored accommodative intraocular lenses in accordance with some embodiments of the disclosed subject matter.

DEFINITIONS

The term "accommodation" as used herein means the ability of a lens to change its focus from distant to near objects.

The term "accommodative" is used herein to describe a replacement lens system and/or a component thereof for implantation in an eye to provide distance vision and accommodation.

The term "biocompatible" is used herein to describe a substance (or an item made therefrom) that neither elicits an unacceptable immune response when implanted in an eye nor elicits an unacceptable change to itself, to other components of the systems and/or the lens assemblies of this invention that have been implanted in the eye, nor to the eye itself.

The terms "centripetal" and "centrifugal" are used herein in lieu of "radially inward" and "radially outward" respectively, and are so used in both classical mechanics and the medical literature.

The terms "cut" and "cutting" when used herein with respect to capsulorhexis are intended to include lasering and tearing as well as actual cutting.

The term "foldable" as used herein includes the rolling, folding, and otherwise elastically reconfiguring spacers, lens assemblies and rings for insertion into an injector.

The term "translation" is used herein as in classical mechanics to describe linear motion. Ophthalmologists use the term "vaulting" to describe the anterior translation of a crystalline or implanted lens, and that is the meaning intended herein.

Medical terms not specifically defined herein are as defined in standard medical dictionaries such as Merriam-Webster's Medical Dictionary.

DETAILED DESCRIPTION OF THE PRESENTLY PREFERRED EMBODIMENTS

The description and the drawings to which the description refers are for purposes of explanation and illustration and are not for limiting the scope of the invention. The scope of the invention is defined by the claims.

Figure 1:
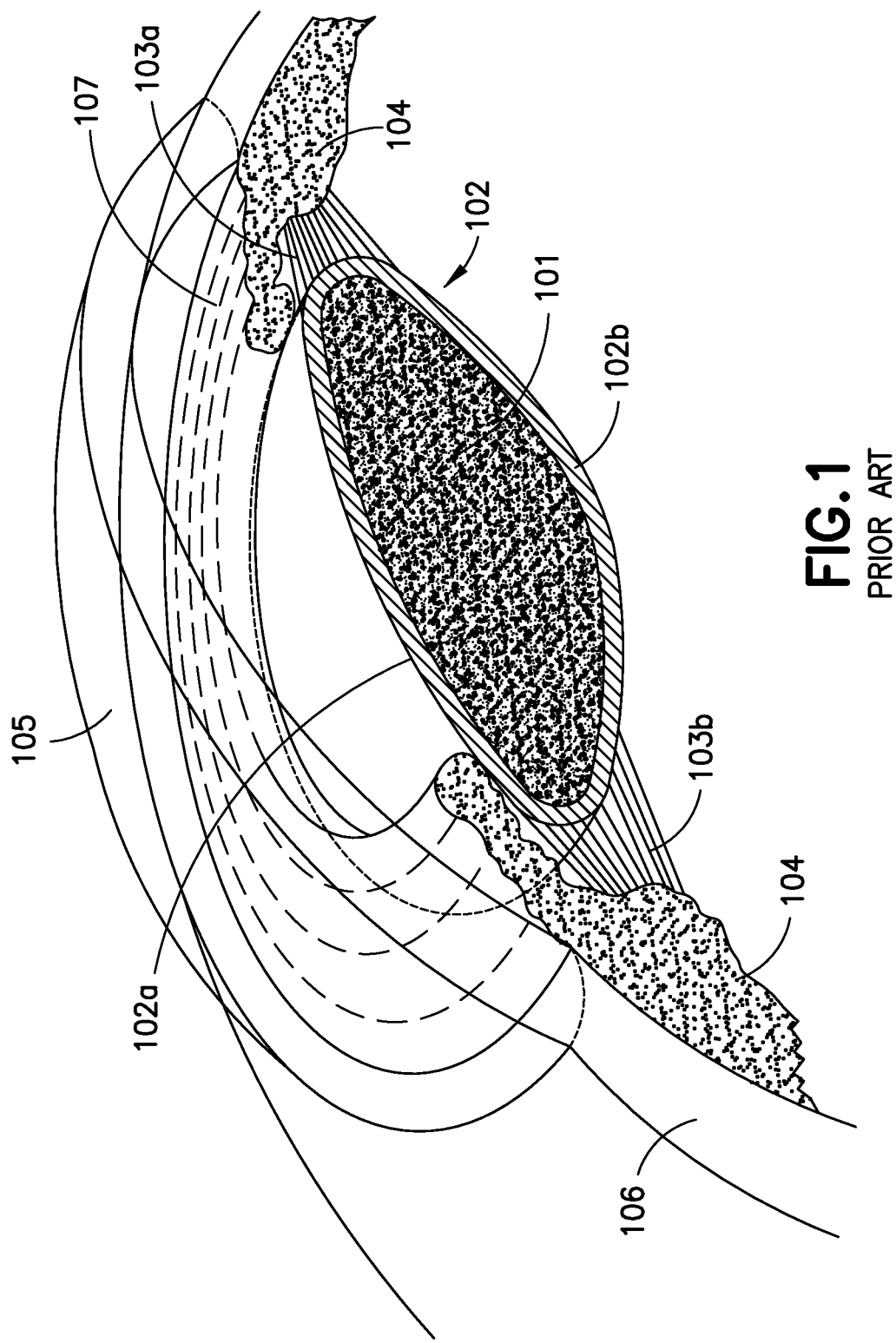
FIG. 1 is a cutaway perspective view of an eye.

FIG. 1 is a cutaway perspective view of an eye according to the prior art, and from which a cataractous or otherwise vision-compromising crystalline lens 101 is to be removed and its function replaced by an intraocular lens. Lens 101 is contained in capsule 102, which comprises anterior capsule 102a and posterior capsule 102b. Anterior capsule 102a includes the part of capsule 102 that is anterior to the equatorial plane of capsule 102, and posterior capsule 102b includes the part of capsule 102 that is posterior to the equatorial plane of capsule 102.

Anterior capsule 102a is connected to ciliary body muscle(s) 104 by anterior zonules 103a and posterior capsule 102b is connected to ciliary body muscle(s) 104 by posterior zonules 103b, and the zonules, according to Helmholtz, act in unison to apply tension to capsule 102, thereby flattening the capsule and the lens for distant vision when muscle(s) 104 are relaxed. Contraction of ciliary body muscle(s) 104, again according to Helmholtz, relaxes the tension on zonules 103 allowing the elastically reconfigurable lens and its capsule to assume the more rounded shape appropriate for the visual accommodation (or at least to do so in a healthy pre-presbyopic eye). FIG. 1 also shows cornea 105, sclera 106, and iris 107.

According to recent studies (e.g., in vivo studies of Croft and in vitro studies of Bernal), at least some, if not all, of the posterior zonules 103b insert at the hyalon membrane before inserting at the anterior capsule, and originate elsewhere on the ciliary body. Thus, the anterior-posterior translation of the posterior capsule is more constrained than that of the anterior capsule, and a decrease in anterior zonular tension not only allows the crystalline lens to assume a more rounded (accommodative) shape, but it also translates the optical center of the crystalline lens anteriorly, and vice versa.

Figure 2:
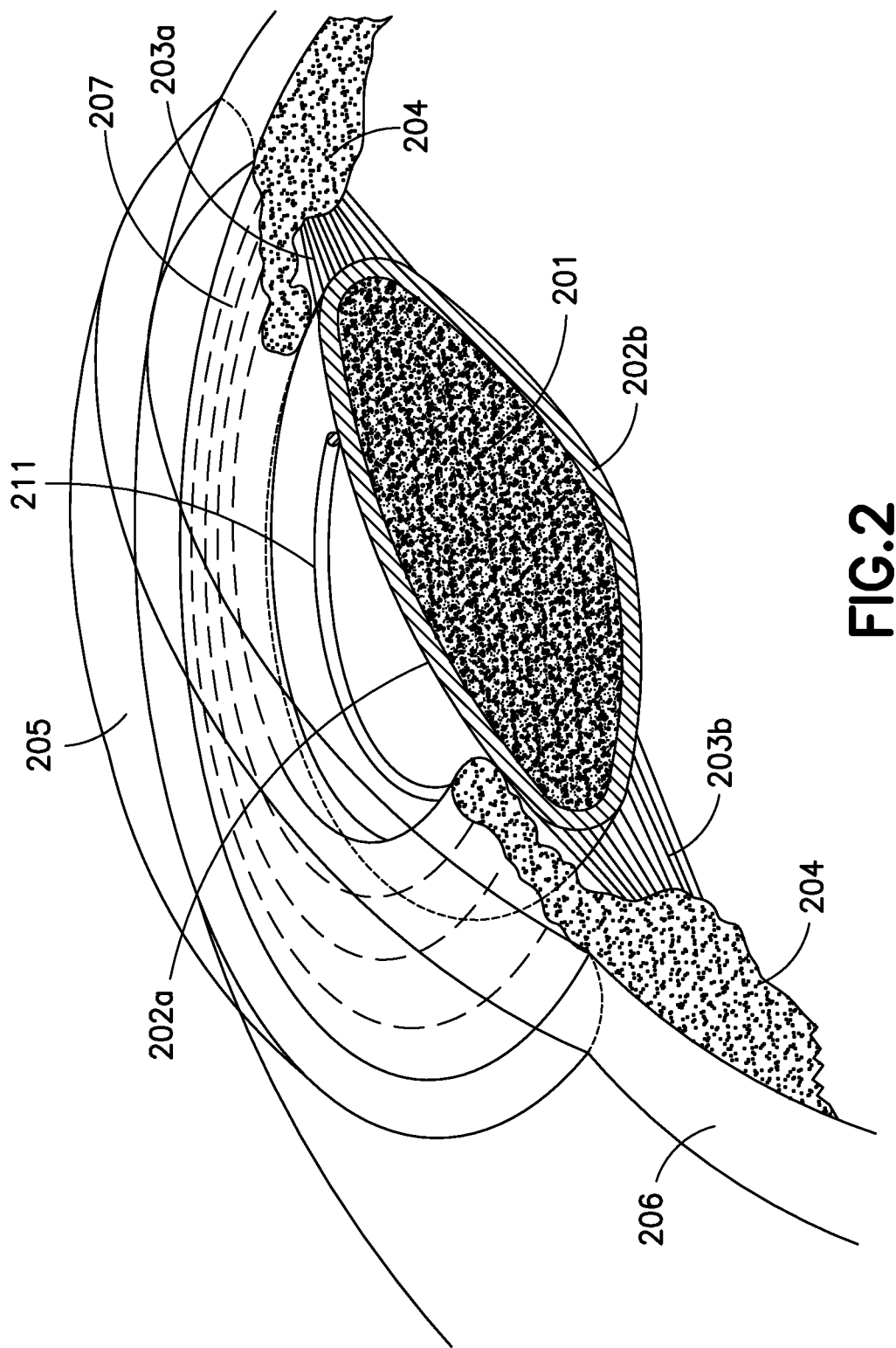
FIG. 2 is the cutaway perspective view of an eye of FIG. 1 into which a tensioning ring has been implanted in accordance with some embodiments of the disclosed subject matter.

FIG. 2 shows substantially axisymmetric tensioning ring 211 that is attached under tension to anterior capsule 202a by at least one of prongs, barbs, hooks, claws and scarring. Ring implantation before capsulorhexis is preferred because the undisturbed capsule is a more stable platform for its implantation, the ring function is best served by a capsulorhexis that is concentric with the ring, and the ring is a convenient template for making it so. FIG. 2 illustrates a step in practicing this invention that is different from the intraocular lens implantation procedures of the prior art.

The steps following attachment of the actuating ring 211 of FIG. 2 are capsulorhexis, extraction of the crystalline lens, purging of surgical debris and implantation of an intraocular lens, and these steps are known and regularly practiced by ophthalmologists, some of whom may prefer to apply a cell growth inhibitor such as Fluorouracil 5 (fu5) to the cut edge of the capsulorhexis.

Some of the accommodative intraocular lenses of this invention also require the implantation of spacers, spacer-actuators, etc.

Figure 4A:
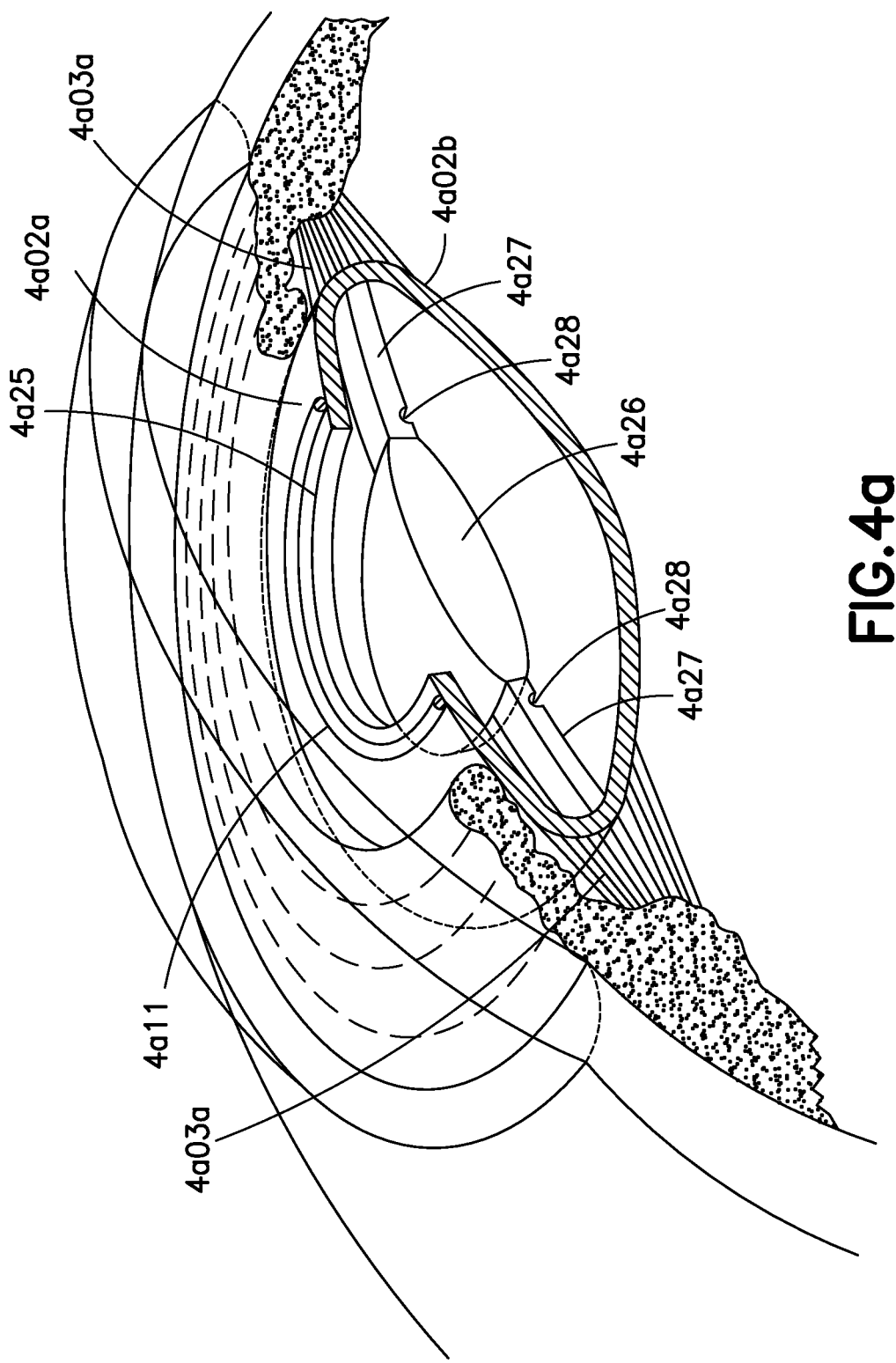
FIGS. 4a-4e are cutaway perspective and sectional views of capsule-equator-anchored accommodative intraocular lenses in accordance with some embodiments of the disclosed subject matter.
Figure 4C:
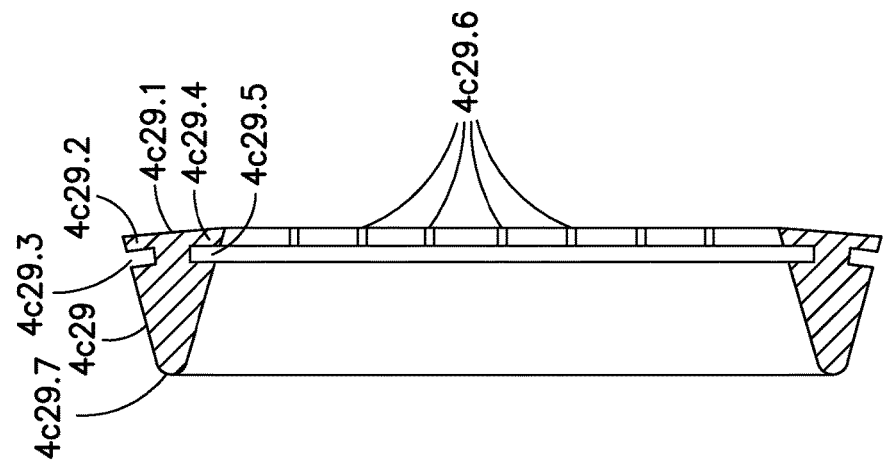
Figure 4B:
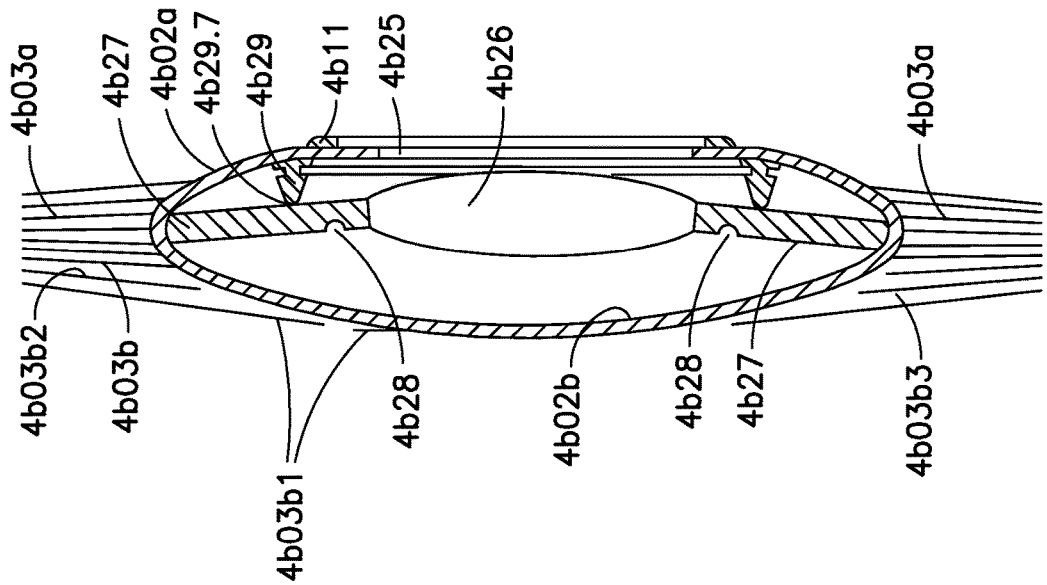
Figure 4E:
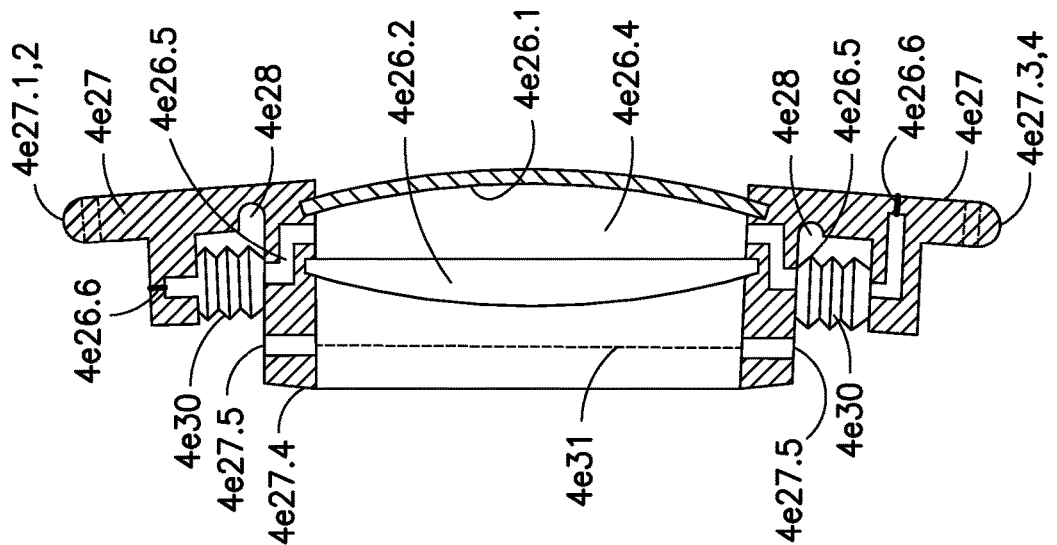
Figure 5D:
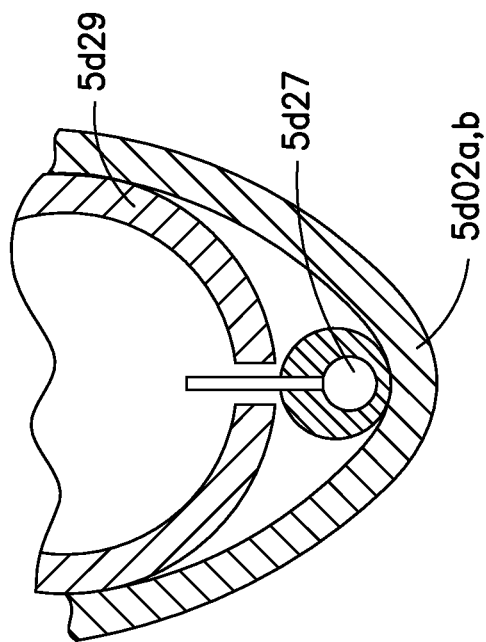
Figure 5C:
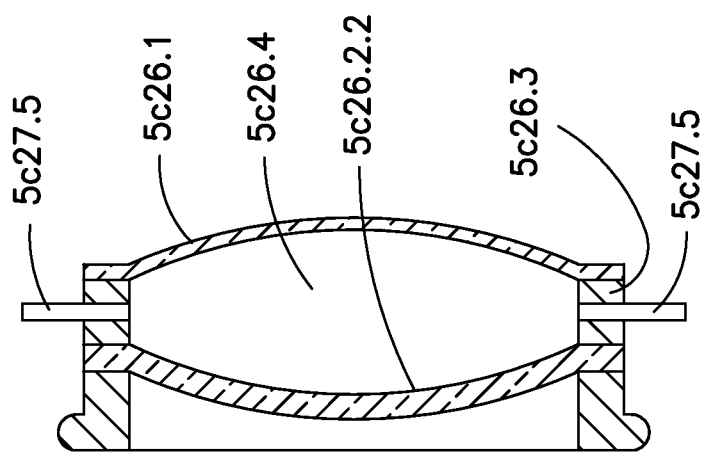
Figure 6A:
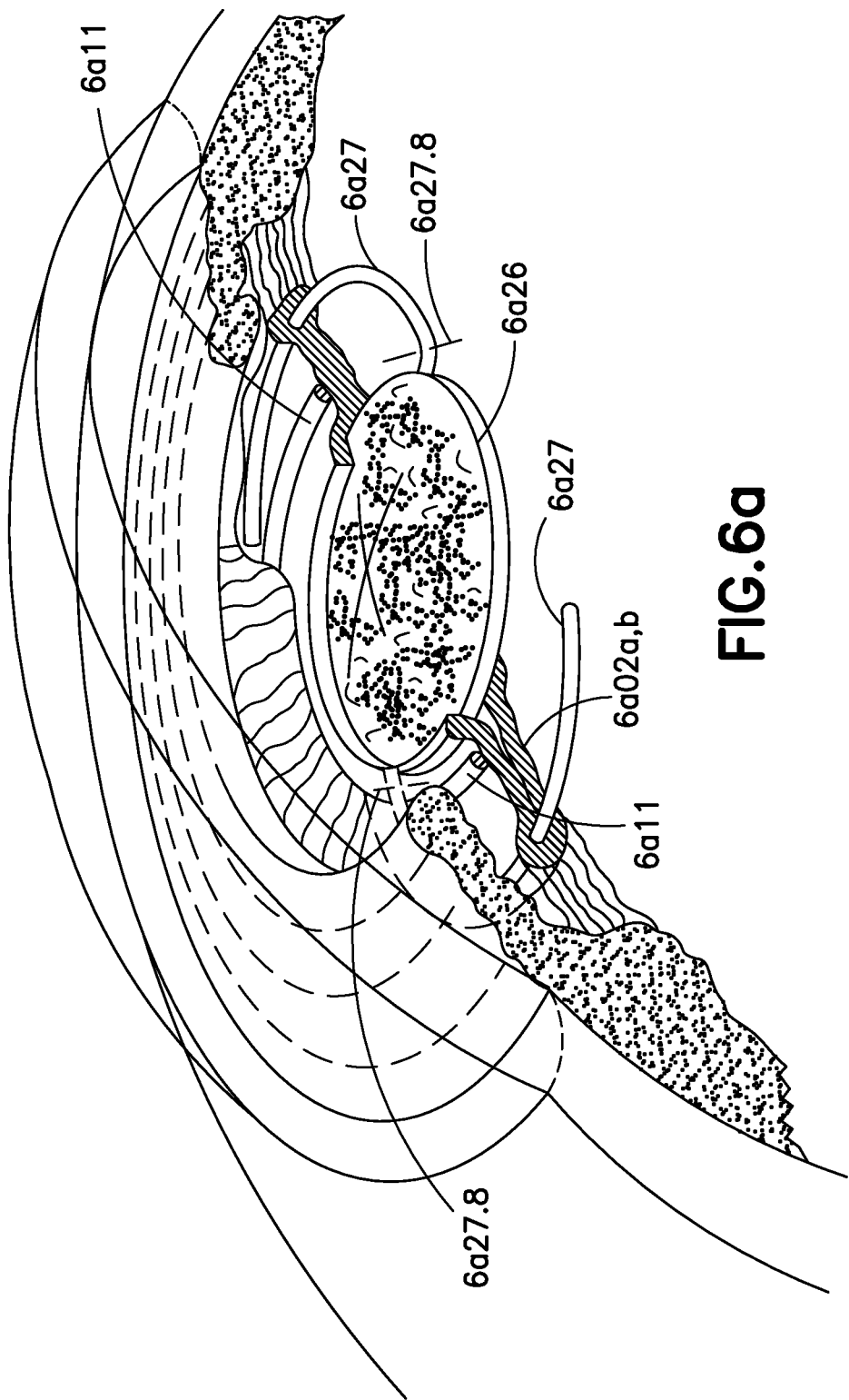
FIGS. 6a-6c are cutaway perspective, plan and sectional views of a defective shrink-wrapped intraocular lens and the details of its replacement in accordance with some embodiments of the disclosed subject matter.
Figure 6B:
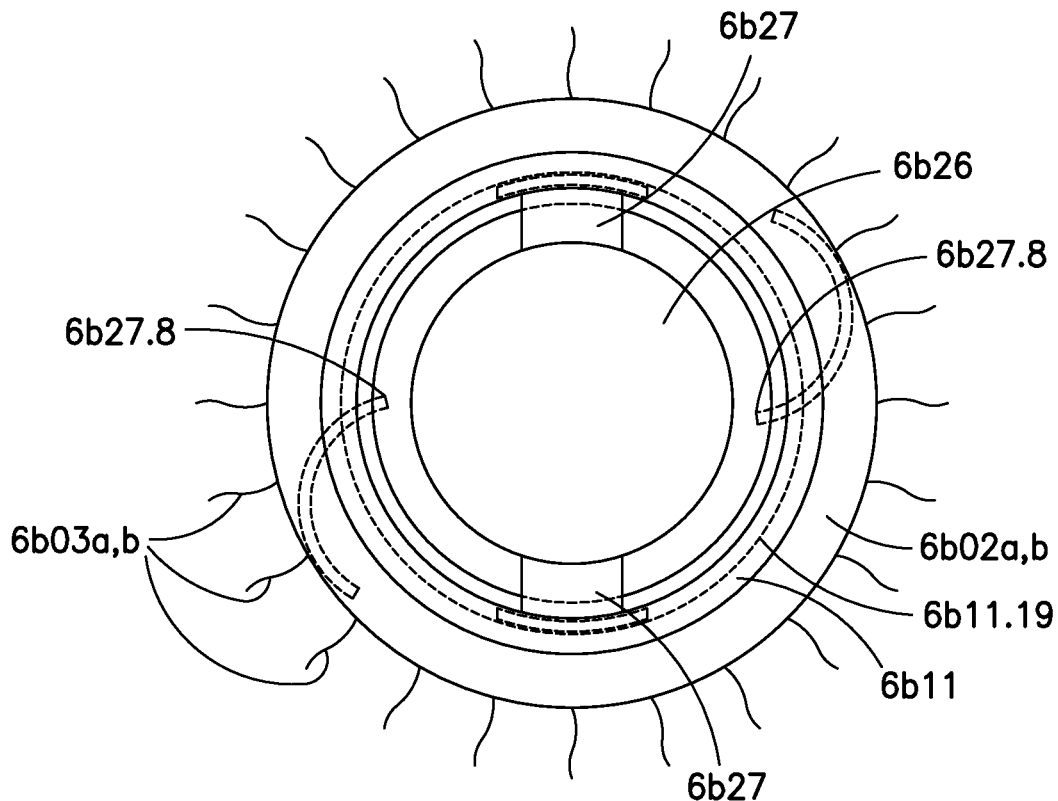

Because extraction of crystalline lens 201 also removes the ultraviolet (UV) protection provided by that lens to parts of the eye (e.g., the retina) that are sensitive to UV, the two-optical-surface lenses 4b26 of FIG. 4b, 4e26.2 of FIG. 4e, 5a26.2 of FIGS. 5e and 6b26 of FIG. 6b and the membrane 5c26.2.2 of FIG. 5c preferably provide the UV protection last by crystalline lens extraction.

Figure 3A:
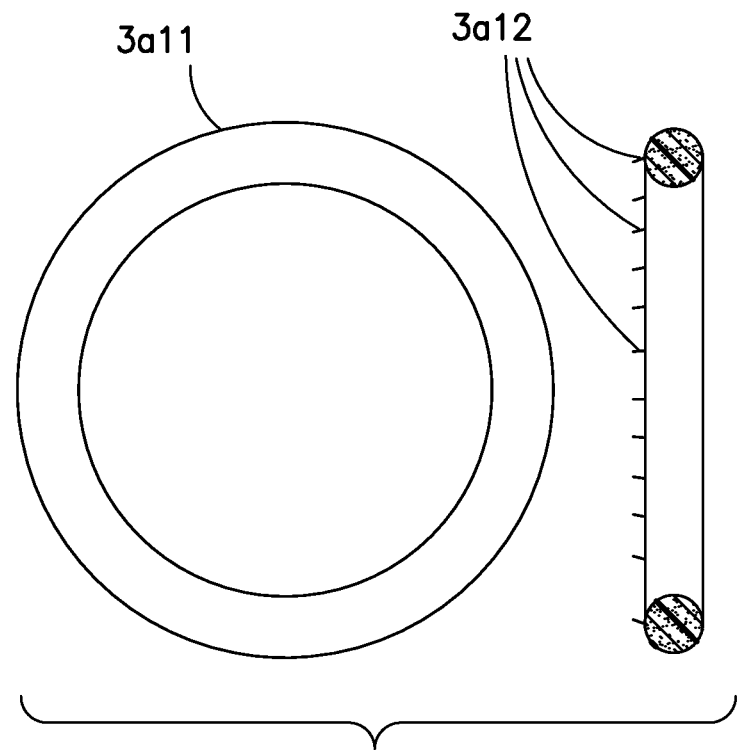
FIGS. 3a-3g are plan and sectional views of rings in accordance with some embodiments of the disclosed subject matter.

FIG. 3a illustrates a toroidal ring 3a11. Toroidal ring 3a11 comprises a biocompatible, elastically reconfigurable material such as a silicone polymer. A plurality of substantially uniformly spaced biocompatible penetrators 3a12 is partially embedded in toroidal ring 3a11 at a uniform angle such that when a portion of the centripetal anterior capsule forces are transferred from the anterior capsule to the ring by capsulorhexis or other means, penetrators 3a12 pierce the anterior capsule and secure the ring to the anterior capsule. That uniform angle is preferably twenty to twenty five degrees because penetrators 3a12 having significantly smaller angles will not be able to serve their intended purpose, and those having significantly larger angles can damage anterior capsule cells at the junction of the penetrators and the ring. Significantly larger angles also increase the risk of capsule damage if the ring is repositioned, replaced or removed.

The penetrators are preferably made of a metal such as that used for stents, and a listing of such metals is contained in Levesque, J. et al., Materials and Properties for Coronary Stents, Advanced Materials and Properties, September 2004 pp 45-48. Of these, nitenol and stainless steel are presently preferred. The penetrators can be hooks, barbs, pins and/or prongs, but the pin-type penetrators shown in the figures are presently preferred because the others can cause more anterior capsule damage not only initially, but even more so if the ring is repositioned.

The pin-type penetrators are preferably sharp enough to penetrate the anterior capsule but blunt enough to push aside the elastic fibers of the anterior capsule rather than puncturing and destroying them as they penetrate the anterior capsule to attach the ring to the anterior capsule. The pin-type penetrators may be also preferably be textured and/or coated to encourage ring retention by the anterior capsule.

Suturing and gluing have also been considered as ways of attaching the rings, but the former introduces an even greater risk of tearing, and no known biocompatible soft tissue glues have an in vivo adhesive life expectancy that is even a small fraction of that of an intraocular lens. Such means of attachment that suitably address these concerns are not, however, excluded from the invention.

Figure 3B:
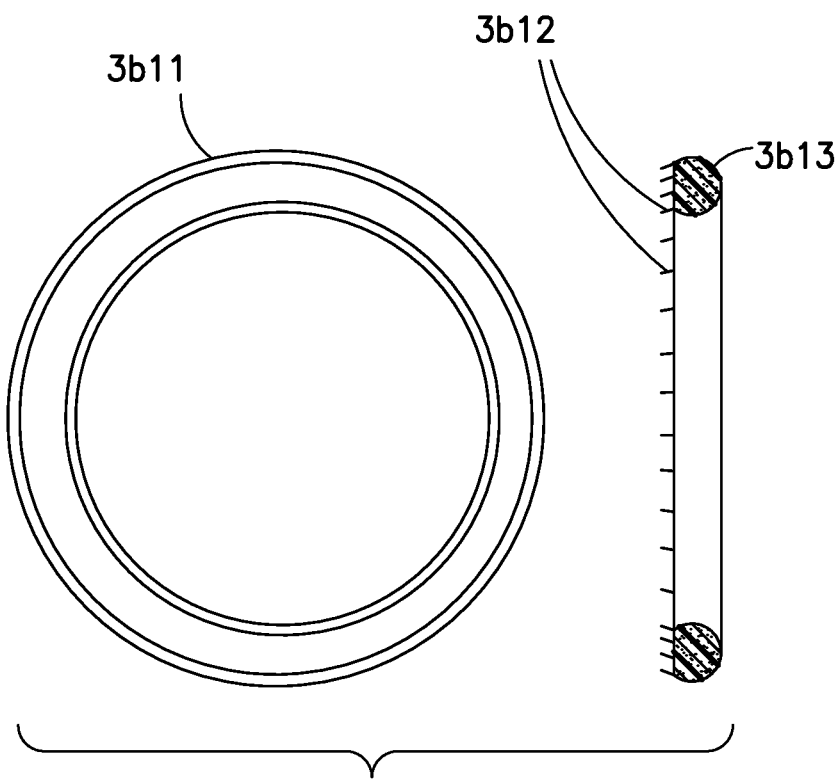

FIG. 3b illustrates a toroid-like ring with a D-shape cross-section. The penetrators are distributed over the flat part of the ring, thereby reducing the risk of tearing.

Figure 3C:
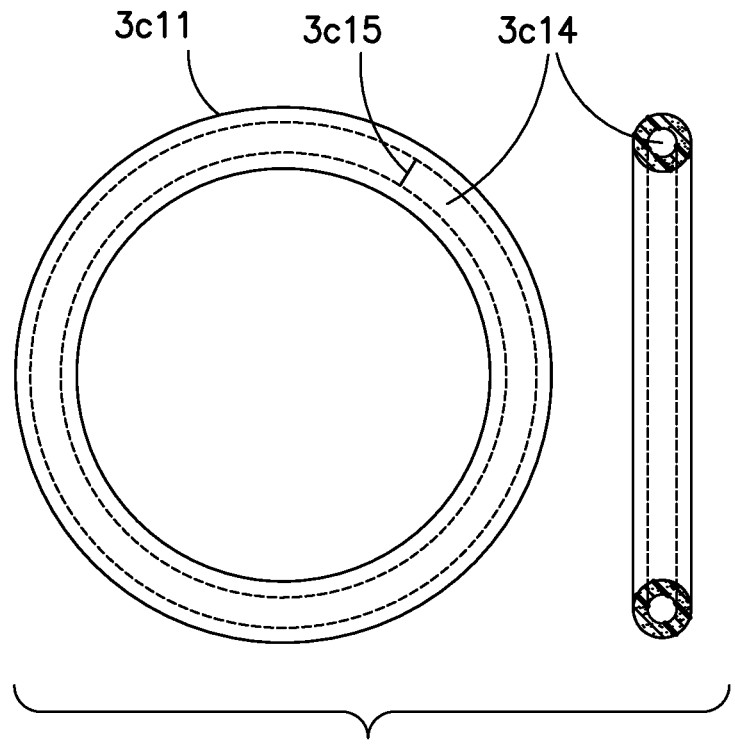

FIG. 3c illustrates a tubular ring 3c11 that has an inner chamber 3c14 that is accessible via an access port 3c15. Ring 3c11 can be used to achieve a desired centripetal force if that provided by rings 3a11 and 3b11 proves to be insufficient. Ring 3c11 also has penetrators but the penetrators have been omitted from the drawing for purposes of clarity of the illustration.

Ring 3c11 is inserted into the eye with inner chamber 3c14 filled with a biocompatible silicone oil, and at a pressure slightly above atmospheric pressure to prevent the influx of fluids from the eye. Once in the eye, it is pressurized with the silicone oil to increase its major diameter to one that corresponds to a desired centripetal force. The ring is then temporarily attached to the anterior capsule with viscoelastic and/or a weak surgical glue and depressurized as appropriate to embed the penetrators.

Figure 3D:
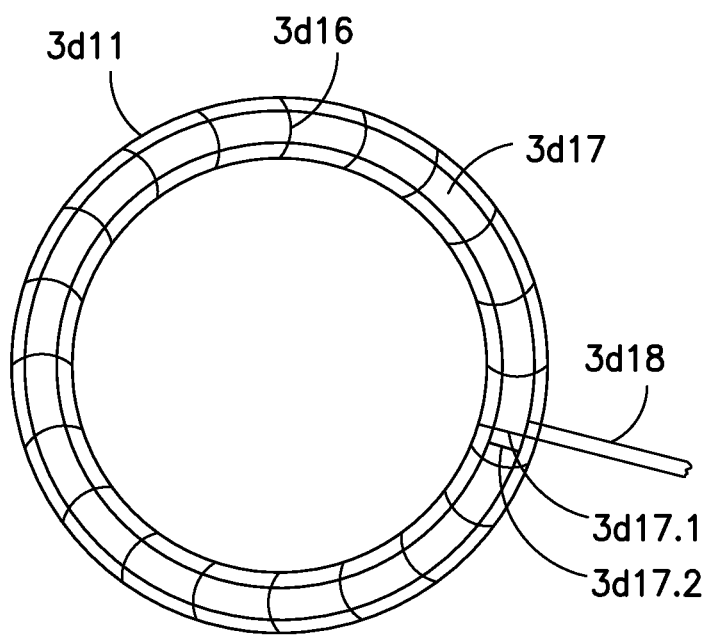
Figure 3G:
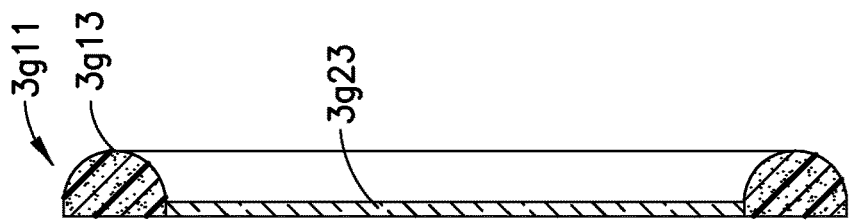
Figure 3F:
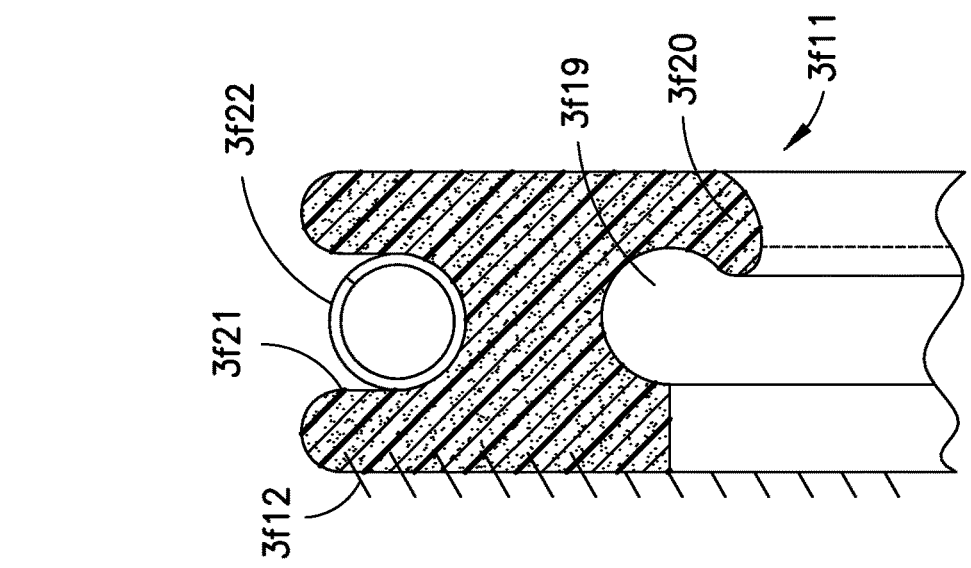
Figure 3E:
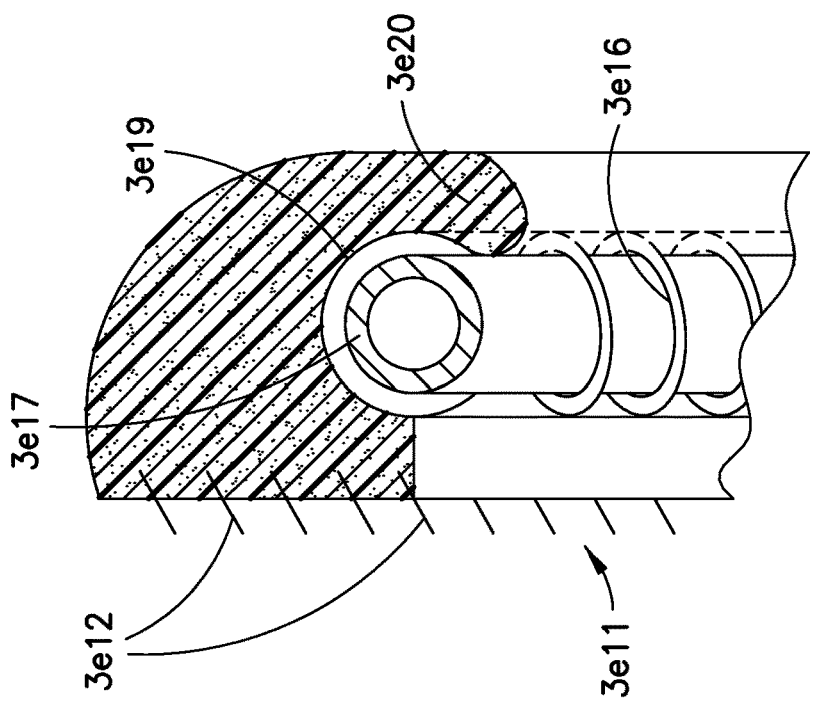

FIG. 3d illustrates an expander ring 3d11 for the anterior capsule tensioning rings of FIGS. 3e and 3f. Expander ring 3d11 comprises a coil spring 3d16 that is closed upon itself, a bladder 3d17 contained within the spring, and a pressurizing tube 3d18. The spring and bladder combination is somewhat analogous to a tube and tire combination in that the bladder is the pressure vessel as is the tube and the spring determines its pressurized shape as does the tire. Thus, when the bladder is pressurized via tube 3d18 or (less conveniently) via an access port such as 3c15 shown in FIG. 3c (not shown in FIG. 3d), the spring constrains the response of the spring/bladder combination to an increase in the major diameter of ring 3d11 (in practice, such spring would likely have its coils wound more tightly than those in the drawing). Suitable spring materials include those used for stents.

The material for bladder 3d17 is preferably an elastically reconfigurable silicone polymer and its shape is ideally a toroidal shell, but the manufacturing complications of winding a spring about such a shell make it more convenient to use tubing or a shell that has been cut and its ends sealed closed. FIG. 3d shows cut ends 3d17.1 and 3d17.2 that are so sealed.

FIGS. 3e and 3f are alternative cross-sections for the ring shown in FIG. 3b. The embodiment of FIG. 3e is much like that of FIG. 3b with the exception of a groove 3e19 for accommodating an expander ring like shown in FIG. 3d. Spring 3e16 and bladder 3e17 are also shown, but the inflation tube corresponding to tube 3d18 of FIG. 3d is not shown. Groove 3e19 also has a lip 3e20, the purpose of which is explained in the descriptions of FIGS. 5b and 6b.

The purpose of the expander ring is to preload the tensioning ring so that it can replace the centripetal anterior capsular forces lost by capsulorhexis. Because bladder 3e17 pressure, and thus the ring tension and diameter, are under control of the surgeon, the ring can be expanded to a diameter appropriate for preliminary positioning on the anterior capsule and reduced enough to implant penetrators 3e12 into the capsule, and the capsulorhexis cut. After the penetrator are implanted into the capsule and the capsulorhexis is cut, the expander ring pressure can be further adjusted to atmospheric pressure, and the expander ring can be removed from both the ring and the eye.

FIG. 3f illustrates groove 3f21 and spring 3f22. The purpose of spring 3f22 is to provide some of the centripetal capsular force that is lost by capsulorhexis and that would otherwise be provided by the ring. A metal spring, however, introduces some restrictions with respect to material selection. because both spring 3f22 and penetrators 3f12 are made of metal, both remain in place and are immersed in the same electrolyte (the aqueous humor), and differences in material introduce the possibility of unintended electrochemical reactions. Thus, spring 3f22 and penetrators 3f12 are preferably made of the same metal to address this possibility.

Ring 3g11 shown in FIG. 3g differs from the previously described rings in that the radially inward capsular force is provided not only by the D-shaped ring portion 3g13, which may be modified in accordance with FIG. 3e, but also by transparent elastically reconfigurable membrane 3g23 attached to it.

Ring 3g11 has penetrators along the flat face of its "D" shaped perimeter as do the rings shown in FIGS. 3b, 3e and 3f, but the penetrators have been omitted from the drawing because including them would erroneously suggest that membrane portion 3g23 also has penetrators, when it does not.

Because ring 3g11 is intended as anterior capsule repair for use with lenses that are elastically reconfigured by the capsule, including lenses taught by Deacon, Terwee and Peyman, it restores not only the radially inward capsular forces lost by capsulorhexis, but also the lens shaping function lost also by capsulorhexis. Membrane 3g23 is for this second purpose thinner at its center than it is at its edge, and has local mechanical properties approximating those of the portion of the anterior capsule it is intended to replace. Typical membrane materials include those used in accommodative intraocular hydraulic lenses.

Membrane 3g23 would, however, block access to the capsules for purposes of capsulorhexis, crystalline lens extraction, and the implantation of lenses, if ring 3g11 were attached to anterior capsules before capsulorhexis. For this reason, ring 3g11 is attached to anterior capsules after some of the above-described steps (e.g., capsulorhexis, removal of crystalline lens, etc.) have been completed.

Regarding the size of the tensioning rings or the external length of penetrators, capsularexii are typically about five millimeters in diameter, crystalline lenses are about six millimeter in diameter, and lens capsules are about ten millimeters in diameter. Thus, allowing for capsulorhexis irregularities, the nominal half millimeter difference in capsule diameter between visual accommodation and disaccommodation, and the risk that the penetrators of rings having major outer diameters approximating that of the capsules can damage the anterior zonules, the presently preferred limits for rings after implantation are major inner diameters of about six millimeters and major outer diameters of about eight millimeters. However, this is not intended to suggest that rings must have these minimum and maximum diameters if rings having smaller maxima and/or different minima are more appropriate for their intended purpose.

Anterior capsules comprise curvilinear radial elastic fibers and circular elastic fibers orthogonal to the radial elastic fibers (an arrangement suggestive of the longitudinal and latitudinal coordinates of a hemispherical shell), and the penetrators are preferably sharp enough to penetrate these capsules but dull enough to push aside the elastic fibers rather than piercing and cutting or otherwise damaging them. These pushed aside elastic fibers will try to return to their previous orthogonal configuration and will thus help to secure the tensioning ring to the anterior capsule, and this securing can be enhanced by contouring, texturing and/or coating the penetrators for maximum effect.

Anterior capsules are also thickest at their equators and thinnest at their poles, and penetrators need to have an external length no more than a few micrometers greater than the portion of the capsule they are intended to penetrate. Their optimal length is best initially determined by in vitro studies and refined on the basis of the experience.

FIG. 4a is a perspective view, partially cut away, of the eye shown in FIG. 2 after capsulorhexis 4a25, the extraction of crystalline lens (e.g., lens 101 shown in FIG. 1), the purging of surgical debris from the eye, and the intracapsular implantation of the accommodative intraocular lens assembly comprising lens 4a26 and haptics 4a27 having bending grooves 4a28.

Accommodation in the embodiment of FIG. 4a is effected by the lens assembly in response to a decrease in tension on anterior zonules 4a03a that results from contraction of the ciliary body muscle(s) and the centripetal forces provided by anterior capsule 4a02a and tensioning ring 4a11, all of which combine to apply centripetal forces to haptics 4a27 that bend the haptics at bending grooves 4a28 to translate (vault) lens 4a26 anteriorly.

The lens assembly of FIG. 4a is also intended as a stand-in for other intraocular lens assemblies intended to be accommodative. Some lens assemblies also serve as shrink-wrap-prevention spacers. No such spacers are shown in FIG. 4a on the assumption that tensioning ring 4a11 and anterior zonules 4a03a will maintain separation between anterior capsule 4a02a and posterior capsule 4a02b.

Even if separation could be so maintained, however, it would be at the risk of the anterior zonule 4a03a stretching, tearing, and/or detaching as mentioned earlier. These risks to the anterior zonules can be addressed by limiting the amount of centripetal force applied to the anterior capsule by tensioning ring 4a11, but this also limits the change in capsule diameter when the ciliary body muscle contracts, thus limiting the change in accommodation as well.

FIG. 4b shows an embodiment that addresses the risks to the anterior zonules of FIG. 4a with a spacer 4b29, which serves as both a spacer with respect to capsule 4b02a,b and an actuator of lens assembly comprising lens 4b26 and haptics 4b27 having bending grooves 4b28, and will be referred to as a spacer-actuator. Spacer-actuator 4b29 is shown in greater detail in FIG. 4c.

Also shown in FIG. 4b are tensioning ring 4b11, anterior capsule 4b02a, anterior capsulorhexis 4b25 through which the crystalline lens and its associated debris has been removed, anterior zonules 4b03a, posterior capsule 4b02b, and posterior zonules 4b03b, 4b03b1, 4b03b2. Some of the posterior zonules are shown as discontinuous to emphasize the point made earlier herein that at least some of the posterior zonules insert at the hyalon membrane (not shown) before inserting at the posterior capsule.

The haptics 4b27 of the lens assembly shown in FIG. 4b have a posterior bias (they are for this reason shown angled towards the left with respect to lens 4b26 in the drawing) so that, in the absence of other forces, the lens will lie in its accommodative (anterior) position, i.e., to the right of the equator of capsule 4b02a,b as shown in the drawing.

When the ciliary body muscle(s) in the natural eye relax to effect disaccommodation the anterior zonules tighten, the anterior capsule flattens, and this flattening both flattens the crystalline lens and translates it posteriorly. This translation is possible in part because the response of the posterior capsule to changes in zonular tension is constrained by the previously mentioned posterior zonular insertion at the hyalon membrane.

Because the centripetal anterior capsule 4b02a forces lost to capsulorhexis have been restored by tensioning ring 4b11, anterior capsule 4b02a will also respond to increased zonular tension by flattening, and this flattening will move spacer-actuator 4b29 posteriorly (to the left in the drawing), bend haptics 4b27 posteriorly at bending grooves 4b28, overcome the posterior bias of the haptics, translate lens 4b26 posteriorly, and effect disaccommodation (and vice versa).

Bending haptic 4b27, however, also risks bending and thus distorting lens 4b26, and while some of this risk is addressed by positioning bending grooves 4b28 proximal to lens 4b26, it may also be appropriate to attach the haptics to a lens support structure as shown in FIG. 4e, instead of directly to the lens. This support structure can also be modified to provide anterior bias in addition to that provided by haptics 4b27 as explained with respect to 4e31 of FIG. 4e.

The anterior face of spacer-actuator 4b29 is in contact with anterior capsule 4b02a, and is contoured accordingly, as shown in greater detail in FIG. 4c. This contour, however, changes with change in anterior zonular tension and this change in contour is addressed by grooves that allow the face of spacer-actuator 4b29 in contact with anterior capsule 4b02a to flex accordingly.

The anterior face of spacer-actuator 4b29 is shown as face 4c29.1 in FIG. 4c, the flex portions of face 4c29.1 as 4c29.2 and 4c29.4, and the grooves defining them as grooves 4c29.3 and 4c29.5, respectively. Depending on the amount of flexing expected, it may also be appropriate to slit the flex portions into flaps via slits 4c29.6. Spacer-actuator 4b29 also has a posterior face 4b29.7 (4c29.7 in FIG. 4c) which presses against haptics 4b27 to effect disaccommodation.

Haptics 4b27 are plate-type haptics that are intended to anchor the lens assembly comprising lens 4b26 and haptics 4b27 having bending grooves 4b28 to the equator of capsule 4b02a,b, and to do so despite a change in capsule diameter resulting from a change in zonular tension, and to do so without compromising the accommodation-disaccommodation mechanism described earlier.

Figure 4D:
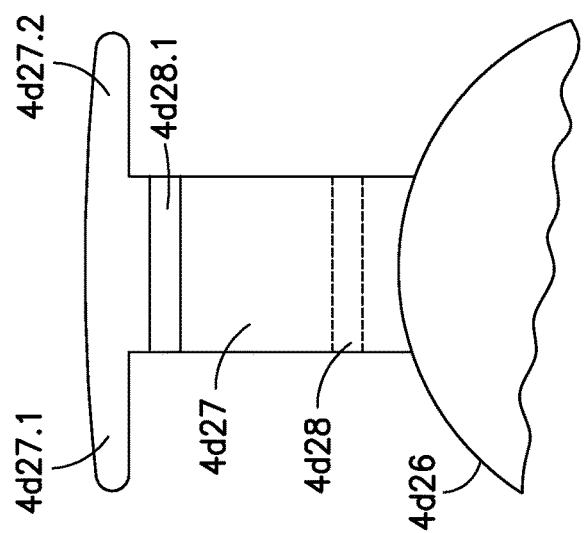

Thus, with reference to FIG. 4d, which is a plan view of the anterior face of the haptic 4b27 in the upper part of FIG. 4b and part of lens 4b26, the haptic is identified by leader line 4d27, its lens-proximal bending groove by leader line 4d28, and the part of the lens by leader line 4d26. Also shown in FIG. 4d are tapered haptic outriggers 4d27.1, 4d27.2 which, like the "J" haptics of conventional intraocular lenses, both allow for differences in capsular equatorial diameter and center the lens in the capsule. The "J" haptics, however, do so only before "shrink-wrapping," something which the spacer function of spacer-actuator 4b29 of FIG. 4b is intended to prevent.

Because the haptic bending mentioned with respect to disaccommodation in the description of FIG. 4b can distort not only lens 4*b*26, but also capsule 4*b*02*a,b* and/or outriggers 4*d*27.1 and 4*d*27.2, an optional second bending groove 4*d*28.1, proximal to outriggers and cut into the anterior face of haptic 4*d*27, is included in the embodiment shown in FIG. 4*b*. Because groove 4*d*28.1 is proximal to both the outriggers and the capsule, it serves the same function with respect to distortion of both the capsule and the outriggers that groove 4*d*28 does with respect to the lens. While only the upper haptic of FIG. 4*b* is shown in FIG. 4*d*, it is clear that both haptics are intended to be the substantially the same, so that if the upper haptic of FIG. 4*b* is modified in accordance with FIG. 4*d*, the lower haptic of FIG. 4*b* would be so modified as well.

While only two haptics spaced 180 degrees apart are shown in FIG. 4*b* and elsewhere herein, an appropriately spaced greater plurality could provide more reliable centering. Outriggers 4*d*27.1 and 4*d*27.2 serve the same function, however, and do so at the cost of less injector space than additional haptic(s) would require.

The translation (vaulting) of lens 4*b*26 provides some degree of visual accommodation as does translation in the human eye, but translational space in both is limited, as is the range of accommodation available therefrom, and most of the accommodative range of the human eye is the result of elastic reconfiguration of the crystalline lens (or by a hydraulic lens after implantation of the embodiment of FIG. 4*e*).

The embodiment shown in FIG. 4*e* is intended as an alternative to translational lens assembly of FIG. 4*b*, and familiar on this basis are haptics 4*e*27 with, of course, bending grooves 4*e*28 and haptic outriggers 4*e*27.1, 4*e*27.2, 4*e*27.3, 4*e*27.4. Outrigger-proximal bending grooves corresponding to grooves 4*d*28.1 of FIG. 4*d* can also optionally be included in the lens assembly shown in FIG. 4*e*.

The lens assembly shown in FIG. 4*e* is, however, both translational and elastically reconfigurable as is the lens in the human eye, and the elastically reconfigurable part of FIG. 4*e* is hydraulic, having transparent elastically reconfigurable membrane 4*e*26.1, fixed focus lens 4*e*26.2, chamber 4*e*26.4 for hydraulic fluid, a support structure for the optical elements of the lens, shown as part of the haptics in the drawing, bellows 4*e*30, hydraulic fluid passages 4*e*26.5 connecting bellows 4*e*30 to chamber 4*e*26.4, and fill/purge ports 4*e*26.6. Membrane 4*e*26.1, lens 4*e*26.2 and bellows 4*e*30 are bonded, glued or otherwise secured to the support structure in ways that allow for their intended function but prevent hydraulic fluid leakage.

Fixed focus lens 4*e*26.2 is shown as planoconvex in the drawing, the plano surface defining the posterior face of chamber 4*e*26.4 and the convex surface providing most of the diopter power needed for disaccommodation, correction of the spherical aberration of a spherical lens of this diopter power, correction of the spherical aberration induced by membrane 4*e*26.1, and, where appropriate, correction of eye anomalies such as myopia, hyperopia and astigmatism.

The fill/purge ports 4*e*26.6 are like access port 3*c*15 of FIG. 3*c*, and are used to fill chamber 4*e*26.4 with a biocompatible hydraulic fluid that also serves as a refractive medium, and to purge air bubbles therefrom. Because that fluid is in contact with lens 4*e*26.2, membrane 4*e*26.1, haptic 4*e*27, and bellows 4*e*30, it should also be compatible with them. Silicone oils used for hydraulic lenses satisfy these requirements and are biocompatible as well.

The diopter power of lens assembly shown in FIG. 4*e* is changed by changing the refractive fluid volume in chamber 4*e*26.4, and thus the curvature of elastically reconfigurable membrane 4*e*26.1, and this is effected by the flexing of haptics 4*e*27 which, in turn, compresses bellows 4*e*30, transferring fluid from bellows 4*e*30 to chamber 4*e*26.4, and thus increasing the curvature of membrane 4*e*26.1 and the diopter power of the lens assembly shown in FIG. 4*e* (and vice versa). Piston-and-cylinder arrangements were also considered as alternatives to bellows as were diaphragms, but bellows are presently preferred because the former introduce the risk of leakage and the latter are of larger diameter and thus require greater actuating force than do the bellows.

The lens assembly shown in FIG. 4*e* is both translational and hydraulically reconfigurable, and may be implanted in the capsule of FIG. 4*b* in lieu of the translation-only lens assembly of FIG. 4*b* to provide a greater range of accommodation than that provided by the latter. The lens assembly of FIG. 4*e* is accommodative when maintained anteriorly within the capsule by the posterior bias of haptics 4*e*27 and disaccommodative when the tension on anterior zonules 4*b*02*a* increases. because anterior capsule 4*b*02*a* is flattened by the tension, and this flattening moves both spacer actuator 4*b*29 and the lens assembly of FIG. 4*e* posteriorly, thereby flexing haptics anteriorly, expanding bellows 4*e*30, removing fluid from chamber 4*e*26.4, decreasing the curvature of membrane 4*e*26.1, and effecting disaccommodation. The lens assembly shown in FIG. 4*e* can be considered a stand-in for other haptic-actuated hydraulic lenses as well.

Hydraulic fluid chamber 4*e*26.4 is, however, also pressurized by elastically reconfigurable membrane 4*e*26.1 as are bellows 4*e*30, and bellows so pressurized apply forces to haptics 4*e*27 in opposition to their intended bias. These hydraulic fluid bellows forces can be addressed by bellows that have an inherent contractional bias, by tension springs (not shown in the drawing) internal to or parallel with the bellows, by forming a portion of the lens assembly proximal to dashed line 4*e*31 as a bellows-type compression spring and by cutting lens assembly shown in FIG. 4*e* at dashed line 4*e*31 and interposing a compression spring (not shown) between the parts separated by the spring.

The lens support structure of FIG. 4*e* is shown as extending posteriorly with respect to lens 4*e*26.2 in order to prevent contact between that lens and the posterior capsule, and the risk that cells can migrate to the surface of that lens, multiply there, and compromise vision. This risk can be further addressed by lens treatments that inhibit cell growth but could compromise posterior capsule cells if a lens so treated contacted that capsule, and the lens structure posterior extension prevents this.

The lens support structure is shown having a posterior face 4*e*27.4, the curvature of which approximates that of the posterior capsule. That structure also has channels 4*e*27.5 to allow for the exchange of aqueous humor that would otherwise be trapped between lens 4*e*26.2 and the posterior capsule during disaccommodation.

Posterior face 4*e*27.4 of FIG. 4*e* and the anterior face 4*c*29 of FIG. 4*c* are both in contact with capsules that are elastic and can thus stretch and/or move with respect to those faces, and the material and/or treatment of those faces should allow for this. Such materials are familiar from their use as, e.g., glaucoma shunts and vascular system repairs.

The lens assemblies of FIGS. 4*b*, 4*e*, and others that may be actuated by tensioning rings such as 4*b*11 and spacer-actuators such as 4*b*29, are implanted into capsules to which tensioning rings have been attached and capsulorhexii cut, and from which crystalline lenses have been extracted and surgical debris purged. The lenses are implanted via injectors that are inserted into the same incision used for crystalline lens extraction, and the lens assemblies are prepared for injection by being rolled and/or folded for insertion into the injectors.

While this rolling and/or folding is a matter of routine for the lens assemblies of FIG. 4b, the lenses of FIG. 4e are bulkier, and injectors large enough to accommodate a full complement of hydraulic fluid may require incisions large enough to require, e.g., surgical corneal repair and correction for corneal distortion. If reducing the complement of hydraulic fluid to a minimum and replacing it via a port readily accessible after implantation, such as the port 4e26.6 nearest the bottom of the lens assembly shown in FIG. 4e, does not adequately address the injector size problem, a more readily foldable fixed focus lens such as membrane lens 5c26.2.2 of FIG. 5c can be substituted for planoconvex lens 4e26.2.

The presently preferred implantation sequence for the embodiments of FIGS. 4b and 4e is lens assembly first and spacer-actuator second, the preferred sequence for rings, capsulorhexii, crystalline lens extraction, and so on, as listed above. It is not, however, intended to preclude alternate sequences that have been practiced successfully by surgeons who prefer them.

Such alternatives include injecting the spacer-actuator first and holding it in place temporarily with viscoelastic, attaching the spacer-actuator to the haptics temporarily or permanently before injection, and forming the spacer-actuator as an integral part of the lens assembly. (If the connection between the spacer-actuator and the lens assembly is permanent, the junction between the two would include a flex groove or its equivalent.)

The crystalline lens in a normal eye remains centered in its capsule because the tension on the elastic fibers of the capsule is axisymmetric when it is centered and asymmetric in a way that acts to center the lens when it is not. The haptic outriggers 4e27.1-4 do the same thing for the lens assemblies of FIGS. 4b and 4e as explained earlier, and the tension on the elastic fibers of the capsule will also center the spacer-actuator for the same reason, but only if the capsulorhexis and the tensioning ring as implanted are substantially axisymmetric with respect to the capsule.

If otherwise, the spacer-actuators of FIGS. 4b and 4e can tilt these lens assemblies and their axes with respect to that of the capsule and thus the eye, and glasses with prismatic correction may be required for proper vision. While connecting the spacer-actuator to the haptics may help to keep the former centered, it does not eliminate the risk of tilt and the need for prismatic correction if the tensioning rings and/or the capsulorhexis are axially asymmetric because the forces applied to the spacer-actuator will still be axially asymmetric.

The accommodative intraocular lens system shown in FIG. 4b may be used if the visual accommodation provided by a translational lens is acceptable. If, however, a greater range of visual accommodation is required, the lens system shown in FIG. 4e may be used. The lens system of FIG. 4b or 4e may not be the best choice, however, if there is a problem with respect to axisymmetry of the tensioning ring and/or the capsulorhexis. If there is such a problem, the embodiments of FIG. 5a (or of FIG. 5a with the lens assembly of FIG. 5c in lieu of that shown in FIG. 5a) may be used.

The lens shown in FIG. 5a is less sensitive to capsulorhexis and/or tensioning ring decentration than the lenses of FIGS. 4b and 4e, but is so at the expense of losing the translational component of the visual accommodation provided by the spacer-actuator of FIG. 4c and haptics 4b27 and 4e27, and of additional complication with respect to implantation.

With reference to FIG. 5a, tensioning ring 5a11 is shown attached to anterior capsule 5a02a, the crystalline lens has been extracted via capsulorhexis 5a25, and a spacer 5a29 has been implanted to maintain a separation between anterior capsule 5a02a and posterior capsule 5a02b (as did the crystalline lens). Spacer 5a29 also serves as a support structure for lens assembly 5a26.

Lens assembly 5a26 comprises an elastically reconfigurable membrane 5a26.1 secured to optical element holder 5a26.3, which is grooved to retain fixed lens element 5a26.2 and ridged to engage the groove in the lens assembly support part 5a29.1 of spacer 5a29.

Thus, a chamber 5a26.4 is formed between membrane 5a26.1 and fixed lens element 5a26.2, and this chamber is filled with a biocompatible hydraulic fluid having an index of refraction higher than that of aqueous humor, as are tubes 5a27.5 and hydraulic lens actuator 5a27, so that when actuator 5a27 is pressurized by tensioning ring 5a11 the curvature of membrane 5a26.1 is increased and accommodation is effected by the increased curvature.

Fixed, plano-convex lens element 5a26.2, which defines one of the boundaries of chamber 5a26.4, includes two optical interfaces: plano interface 5a26.2.1 in contact with the previously mentioned hydraulic fluid and convex interface 5a26.2.2 in contact with the aqueous humor. In one embodiment, the fixed lens surface 5a26.2.2 is configured to provide, among other things, (1) most of the disaccommodation diopter power previously provided by the crystalline lens, (2) correction for corneal distortions such as astigmatism, (2) correction for the spherical aberration typical of hydraulic lenses, and (3) correction for the spherical aberration of high diopter spherical lenses. The plano interface can be replaced with a curved surface that provides at least some of the magnification and/or correction, if appropriate.

Spacer 5a29 has an equatorial diameter less than that of anterior and posterior capsules 5a02a, 5a02b, a contour approximating that of the capsule of a natural eye with the exception of its diameter, and a stiffness adequate to maintain that contour despite forces that are exerted by anterior zonules 5a03a, posterior zonules 5a03b (some of which are shown as discontinuous for reasons mentioned earlier herein), equatorial zonules 5a03e, and tensioning ring 5a11. Spacer 5a29 also has an anterior circular axisymmetric opening 5a29.5 of a diameter that is greater than that of capsulorhexus 5a25 and an optional axisymmetric posterior opening 5a29.6.

FIG. 5b illustrates the interaction between tensioning ring 5b11 and actuator 5b27. Actuator 5b27 is held in place with respect to ring 5b11 by groove 5b19 and lip 5b20 and has a thin-walled portion 5b27.1 and thick-walled portion 5b27.2. When ring 5b11 contracts, the thin-walled portion 5b27.1 of actuator 5b27 is urged toward thick-walled portion 5b27.2, causing some of the refractive hydraulic fluid to flow from the actuator to hydraulic lens assembly 5a26 via tube(s) 5a27.5, increasing the curvature of membrane 5a26.1, and effecting accommodation thereby. Tensioning ring 5b11 also has actuator-contacting surfaces 5b11.1 appropriately curved to facilitate this.

Also shown in FIG. 5b are penetrators 5b12, a fill port 5b27.6 (which is analogous to access port 3c15 of FIG. 3c), a connection nipple 5b27.4 for connection to a tube 5a27.5 of FIG. 5a (the connection nipple can, in the alternative, be the tubing itself), and bypass channels 5b11.5 which address the possibility that tensioning ring 5b11 may contact some part of the eye anterior to ring 5b11, such as the iris, and obstruct the aqueous humor drainage path.

Accommodation is at least in part effected by: (1) the tension on anterior zonules 5a03a and thus the centrifugal forces applied to anterior capsule 5a02a, both being reduced by contraction of the ciliary body muscle(s) as is the tension on tensioning ring 5a11, the part of the anterior capsule not removed by capsulorhexus serving as the coupling between the unaltered parts of the eye and the man-made parts introduced to restore both distant and accommodative vision. The changes in tension also change the equatorial diameter of the capsule, and the equatorial diameter of spacer 5a29 is smaller than that of capsule 5a02a,b to allow for this. Because the change in tension also involves relative motion between anterior capsule 5a02a and spacer 5a29, it is important (1) that penetrators 5b12 do not engage spacer 5a29 (the diameter of anterior opening 5a29.5 is made larger than that of ring 5a11 for this reason), (2) that capsule 5a02a,b does not adhere to spacer 5a29, and (3) that the material of spacer 5a29 and/or its coating is selected accordingly.

The lens assembly shown in FIG. 5c (which is an alternative to 5a26) comprises support structure 5c26.3, refractive hydraulic fluid chamber 5c26.4 and tubes 5c27.5 (which were previously mentioned as an alternative to nipple(s) 5b27.4). The planoconvex lens 5a26.2 of FIG. 5a has, however, been replaced by transparent membrane 5c26.2.2, which, in conjunction with the refractive hydraulic fluid in chamber 5c26.4, provides most, if not all, of the diopter power needed for distance vision, and also correction for the aberrations mentioned earlier. Because membrane 5c26.2.2 is intentionally made thicker than hydraulic lens membrane 5c26.1, it is unyielding at the hydraulic pressures that actuate hydraulic lens assembly of FIG. 5c and thus determines the curvature of a fixed focus refractive hydraulic fluid lens, but allows for more compact folding for insertion into an injector. The fixed focus refractive hydraulic fluid lens defined by membrane 5c26.2.2 can also provide the corrections mentioned with respect to lens surface 5a26.2.2.

Because the lens assembly of FIG. 5c has no two-optical-surface lenses corresponding to lens 5a26.2 of FIG. 5a to provide UV filtration, that protection is provided by, e.g., suitably modified membrane 5c26.2.2, hydraulic fluid 5c26.4, or both.

FIG. 5d shows actuator 5d27 interposed between capsule 5d02a,b and spacer 5d29, where it is intended to be actuated by the change in capsule equatorial diameter.

Assuming that capsule 5a02a,b of FIG. 5a has been prepared for the implantation of spacer 5a29 and lens assembly 5a26 of FIG. 5a or that of FIG. 5c by attachment of tensioning ring 5a11, capsulorhexis, and the purging of surgical debris, the preferred implantation sequence for these assemblies includes (1) implanting spacer 5a29 first, (2) implanting a lens assembly that has been prepared for implantation by attachment of tubes 5a27.5 or 5c27.5 and hydraulic lens actuator 5a27 and filling the assembly with hydraulic fluid and the purging of bubbles therefrom, (4) inserting hydraulic actuator 5a27 into the groove in tensioning ring 5a11 corresponding to groove 5b19 of FIG. 5b, and (5) adjusting the hydraulic fluid pressure, and thus the curvature of hydraulic membrane 5a26.1 or 5c26.1, via the port corresponding to 5b27.6 of FIG. 5b. If spacer 5a29 can be folded small enough for implantation with lens assembly 5a26 or that of FIG. 5c secured thereto or an integral part thereof, they would be so implanted.

The preferred procedures for the implantation of the accommodative intraocular lens systems of FIG. 4b, the system in which the lens assembly of FIG. 4b is replaced with the lens assembly of FIG. 4e, and those of FIG. 5 include the attachment of the tensioning ring to the anterior capsule before capsulorhexis and crystalline lens extraction for reasons explained with respect to FIG. 2 (see paragraph 52), and these procedures thus introduce the risks to the anterior zonules mentioned with respect to FIG. 4a (see paragraph 78).

While these risks are addressed by the spacer-actuators of the systems shown in FIGS. 4a and 4e and the spacers of those of FIG. 5, they are not so addressed until these spacer-actuators and spacers are implanted. It is therefore appropriate to employ grooved tensioning rings such as those of FIG. 4e, 4f, or 5b, and to leave the expander rings, such as the one shown in FIG. 3d, in those grooves after attaching the tensioning rings to the anterior capsules, but at a pressure corresponding to tensioning ring centripetal forces that are safe for the zonules of empty capsules, until the spacer-actuators or spacers are implanted. The expander rings may then be depressurized and removed from both the tensioning rings and the eye.

FIG. 6a shows an "off-label" use of the tensioning rings of the invention in which a grooved tensioning ring 6a11 is attached to shrink-wrapped capsule 6a02a,b to provide for the attachment of a new intraocular lens to augment or to replace an existing intraocular lens. Existing lens 6a26 is shown as clouded in FIG. 6a, and if the existing lens is to be removed for this or other reasons it is removed by cutting haptics 6a27 at dashed lines 6a27.8 and extraction by means familiar to surgeons skilled in the art.

FIG. 6b is a plan view of the shrink-wrapped capsule 6a02a,b of the eye shown in FIG. 6a after clouded lens 6a26 has been extracted, tensioning ring 6b11 has been attached to shrink-wrapped capsule 6b02a with the aid of an expander ring and the procedures described herein, and replacement intraocular lens assembly comprising lens 6b26 and haptics 6b27 has been secured to tensioning ring 6b11 by inserting haptics 6b27 into tensioning ring groove 6b11.19 (analogous to grooves 3e19 or 3f19 of FIGS. 3e and 3f, respectively).

Also shown in FIG. 6b are anterior and posterior zonules 6b03a,b, capsule 6b02a,b and the "J" haptics of FIG. 6a and their cut ends (shown dashed in FIG. 6b and identified by leader lines 6b27.8).

Figure 6C:
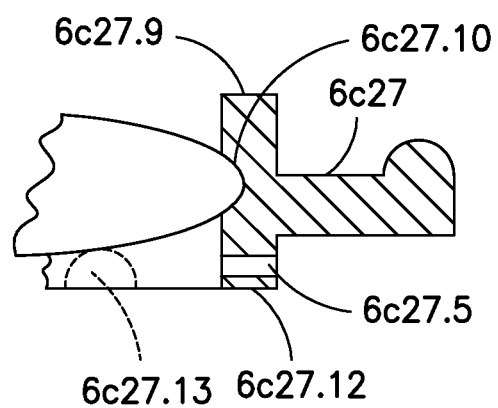

The outboard ends of haptics 6b27 are contoured to engage tensioning ring groove 6b11.19, and this haptic contour is shown in greater detail in FIG. 6c, which is a sectional view of one of the haptics 6b27 and of a part of lens 6b26. The inboard portion of haptics 6b27 is a lens support structure identified by leader line 6c27.9 in FIG. 6c, and that structure has a lens groove 6c27.10, a skirt portion 6c27.12, and aqueous humor channel 6c27.5 analogous to 4e27.5 of FIG. 4e.

Skirt 6c27.12 is preferably long enough to maintain a separation between lens 6b26 and eye tissue to discourage cell migration, and because of that separation, the lens can be coated and/or impregnated with a cell growth inhibitor. Skirt 6c27.12 can also be contoured as represented by cutaways 6c27.13 to allow for irregularities such as those resulting from the remaining portions of the haptics shown in FIG. 6a, and if so, cutaways 6c27.13 can also serve as drainage channels, and aqueous humor channel(s) 6c27.5 can be omitted.

If lens assembly of 6b26 and 6b27 is intended to complement rather than replace introcular lens 6a26 of FIG. 6a, its skirt can be made long enough to allow clearance between the lenses as well.

The biocompatibility of the rings of this invention has been earlier addressed. One way to effect the compatibility of the rings with respect to other components of the lens systems of this invention, such as spacers, spacer-actuators, lenses, lens support structures, haptics, hydraulic lens actuators, etc. (not only to one another but also with respect to the eye when implanted therein), is to make all of the lens system components and their parts (with the exception of the ring penetrators and springs) of a same class of biocompatible polymer, which may be compounded and cured to provide, among others, the stiffness, elastic reconfigurability, transparency, and index of refraction that are appropriate for the component and the parts thereof.

The majority of intraocular lenses that are commercially available have silicone polymer lenses and silicone polymer haptics that have proven themselves to be viable in the eyes millions of patients, and these polymers, suitably modified to provide the optical and other physical properties mentioned above, can be used for the components and parts of the lens systems of this invention.

Thus, the rings of this invention, their uses, and accommodative intraocular lens systems made functional by their use have been illustrated and described. The methods and procedures for the implantation of these rings and those peculiar to the lens systems of this invention have also been described. The methods and procedures for extraction of compromised crystalline lenses are known, and are routinely practiced. The methods and procedures for extraction of compromised intraocular lenses are also known.

While the tensioning rings of this invention are shown as attached to the anterior faces of the anterior capsules in FIGS. 2, 4 and 5, there is nothing that inherently precludes their attachment to the posterior face of the anterior capsules (which can be done after capsulorhexis and crystalline lens extraction) or a "U" section ring that attaches to both, and such embodiments are within the scope of this invention.

What is claimed is:

1. A tensioning device for external attachment to an anterior capsule of an eye and placement proximal to and radially outward with respect to an anterior capsulorhexis site thereof, the device comprising:
   a substantially axisymmetric, biocompatible, elastically reconfigurable tensioning ring for restoring at least a portion of anterior capsule centripetal forces lost, or to be lost, by the capsulorhexis; and
   a plurality of biocompatible penetrators used to attach the tensioning ring to the anterior capsule, wherein the plurality of penetrators is partially embedded in a part of the tensioning ring for facing the anterior capsule, wherein the penetrators are oriented to penetrate the anterior capsule when the tensioning ring is attached to the anterior capsule by insertion of the penetrators into the anterior capsule from a direction outside of the eye and towards an interior of the eye, and wherein the tensioning ring is configured to be placed closer to an opening created by the capsulorhexis than to an equator of the anterior capsule.

2. The tensioning device of claim 1, wherein the tensioning ring is made at least in part of a silicone polymer.

3. The tensioning device of claim 1, wherein a cross section of the tensioning ring is one of circular, tubular, and D-shaped.

4. The tensioning device of claim 1, wherein the penetrators partially embedded in the part of the tensioning ring configured for facing the anterior capsule are substantially uniformly spaced apart from one another and embedded at substantially the same angle with respect to a principal axis of the tensioning ring.

5. The tensioning device of claim 1, wherein the plurality of penetrators is sufficiently sharp to penetrate the anterior capsule and blunted enough to minimize damage to elastic fibers of the anterior capsule.

6. The tensioning device of claim 1, wherein the plurality of penetrators is at least one of coated and textured.

7. The tensioning device of claim 1, wherein the plurality of penetrators comprises a set of at least one of pins, hooks, barbs, and prongs.

8. The tensioning device of claim 1, wherein a part of the tensioning ring proximal to a principal axis of the ring comprises a substantially axisymmetric groove configured to hold at least one of an expander ring, a hydraulic lens actuator, and haptics of an intraocular lens.

9. The tensioning device of claim 8, wherein the groove is configured to hold the expander ring, wherein the expander ring is configured for a temporary insertion into the groove and wherein the expander ring comprises a coil spring closed upon itself, a bladder contained within the spring, and at least one of a pressurizing tube and an access port for pressuring and depressurizing the bladder.

10. The tensioning device of claim 1, wherein the plurality of biocompatible penetrators are all made of a particular biocompatible metal, and wherein a part of the tensioning ring distal from a principal axis of the tensioning ring comprises a substantially axisymmetric groove contained within which is a tensioning spring, the tensioning spring being made of the same biocompatible metal as all of the plurality of penetrators are made of.

11. The tensioning device of claim 1, wherein the tensioning ring further comprises a transparent, elastically reconfigurable membrane, wherein the membrane is made of a biocompatible material, and wherein the membrane is affixed to the tensioning ring substantially axisymmetrically with respect to a principal axis of the ring.

12. The tensioning device of claim 11, wherein the membrane further comprises mechanical properties substantially similar to mechanical properties of an anterior capsule portion that is removed by the capsulorhexis.

13. The tensioning device of claim 12, wherein all of the plurality of penetrators are made of a particular biocompatible metal, the particular biocompatible metal being one of nitinol and stainless steel.

14. The tensioning device of claim 1, further comprising at least one bypass channel arranged for facilitating a flow of aqueous humor from a face of the ring distal from a principal axis of the ring to a face proximal to the principal axis.

* * * * *